United States Patent
Buck et al.

(10) Patent No.: US 9,649,295 B2
(45) Date of Patent: May 16, 2017

(54) CHEMICAL INHIBITORS OF SOLUBLE ADENYLYL CYCLASE (SAC)

(75) Inventors: Jochen Buck, Greenwich, CT (US); Lonny R. Levin, New York, NY (US); Fritz A. Muhlschlegel, Canterbury (GB)

(73) Assignees: Cornell Research Foundation, Inc., Ithaca, NY (US); Kent University, Canterbury (GB)

( * ) Notice: Subject to any disclaimer, the term of this patent is extended or adjusted under 35 U.S.C. 154(b) by 1406 days.

(21) Appl. No.: 10/586,929

(22) PCT Filed: Jan. 20, 2005

(86) PCT No.: PCT/US2005/001807
§ 371 (c)(1),
(2), (4) Date: May 24, 2007

(87) PCT Pub. No.: WO2005/070419
PCT Pub. Date: Aug. 4, 2005

(65) Prior Publication Data
US 2007/0244174 A1    Oct. 18, 2007

Related U.S. Application Data

(60) Provisional application No. 60/537,864, filed on Jan. 21, 2004.

(51) Int. Cl.
*A61K 31/415* (2006.01)
*A61K 31/4184* (2006.01)
*C12Q 1/527* (2006.01)

(52) U.S. Cl.
CPC ........ *A61K 31/415* (2013.01); *A61K 31/4184* (2013.01); *C12Q 1/527* (2013.01); *G01N 2333/988* (2013.01)

(58) Field of Classification Search
CPC .............. A61K 31/4184; A61K 31/415; C07D 235/04; C07D 235/28; C07D 235/32
See application file for complete search history.

(56) References Cited

U.S. PATENT DOCUMENTS 6,132,957 A * 10/2000 Johnson et al. .................. 435/4
6,544,768 B1    4/2003 Buck et al.

FOREIGN PATENT DOCUMENTS

WO        01/21829 A1    3/2001
WO        01/85753 A1    11/2001

OTHER PUBLICATIONS

Bailey et al 'Adherence of Candida albicans to Human Buccal Endothelial Cells: Host-Induced Protein Synthesis and Signaling Events' Infection and Immunity, 63(2), p. 569-572, 1995.*
Rosenthal, P. 'Plasmodium falciparum: Effects of Proteinase inhibitors on Globin Hydrolysis by cultured Malaria Parasites' Experimental Parasitology, vol. 80, p. 272-281, 1995.*
Naik et al 'Synthesis and characterization of niobium(V) complexes with terdentate ONO donor hydrazones' Indian Journal of Chemistry, vol. 41A, p. 780-784, 2002.*
Qiao, J., et al., "Cell Cycle-Dependent Subcellular Localization of Exchange Factor 30 Directly Activated by CAMP", J. Biol. Chem. (2002), vol. 277:29, pp. 26581-26586.
Read, L. K. et al., "Plasmodium falciparum-Infected Erythrocytes Contain an Adenylate Cyclase with Properties Which Differ from the Host Enzyme", Molecular & Biochemical Parasitology (1991), vol. 45, pp. 109-119.
Renström, E., et al., "Protein Kinase A-Dependent and -Independent Stimulation of Exocytosis by cAMP in Mouse Pancreatic B-Cells", J. Physiol. (1997), vol. 502:1, pp. 105-118.
Raibowol, K. T., et al., "Microinjection of the Catalytic Subunit of CAMP-dependent Protein Kinase Induces Expression of the c-fos Gene", Cold Spring Harb. Symp. Quant. Biol. (1988), vol. 53, pp. 85-90.
Raibowol, K. T., et al., "The Catalytic Subunit of CAMP-Dependent Protein Kinase Induces Expression of Genes Containing CAMP-Responsive Enhancer Elements", Nature (1988), vol. 336, pp. 83-86.
Rich T. C., et al., "Cyclic Nucleotide-Gated Channels Colocalize With Adenylyl Cyclase in Regions of Restricted cAMP Diffusion", J. Gen. Physiol. (2000), vol. 116:2, pp. 147-161.
Rich, T. C., et al., "A Uniform Extracellular Stimulus Triggers Distinct cAMP Signals in Different Compartments of a Simple Cell", Proc. Natl. Acad. Sci. USA (2001), vol. 98:23, pp. 13049-13054.
Roelofs, J., et al., "Deducing the Origin of Soluble Adenylyl Cyclase, A Gene Lost in Multiple Lineages", Mol. Biol. Evol. (2002), vol. 19:12, pp. 2239-2246.
Rutter, G. A. "Nutrient-Secretion Coupling in the Pancreatic Islet Beta-Cell: Recent Advances," Mol. Aspects Med. (2001), vol. 22, pp. 247-284.

(Continued)

Primary Examiner — Craig Ricci
Assistant Examiner — Christopher R Stone
(74) Attorney, Agent, or Firm — Fox Rothschild LLP

(57) ABSTRACT

The present invention relates to a method of treating a disorder mediated by soluble adenylyl cyclase in a subject. The method involves administering to a subject an effective amount of a compound disclosed herein that modulates soluble adenylyl cyclase, under conditions effective to treat the disorder mediated by soluble adenylyl cyclase. The present invention also relates to a method of treating a disorder mediated by soluble adenylyl cyclase in a subject, where the disorder is selected from the group consisting of: learning or memory disorders, malaria, fungal infection, spinal cord injury, Alzheimer's disease, amyotrophic lateral sclerosis, and peripheral neuropathy. The method involves modulating soluble adenylyl cyclase in the subject. Another aspect of the present invention relates to a method of modulating soluble adenylyl cyclase. The method involves contacting eukaryotic cells with a compound that modulates soluble adenylyl cyclase, under conditions effective to modulate soluble adenylyl cyclase.

5 Claims, 19 Drawing Sheets

(56) References Cited

OTHER PUBLICATIONS

Salehi, A. et al., "Alzheimer's Disease and NGF Signaling", J. Neural Trans. (2004), vol. 111, pp. 323-345.
Schubart, U. K., et al., "Cyclic Adenosine 3':5'-Monophosphate-Mediated Insulin Secretion and Ribosomal Protein Phosphorylation in a Hamster Islet Cell Tumor", J. Biol. Chem. (1977), vol. 252:1, pp. 92-101.
Shibasaki, T., et al., "Interaction of ATP Sensor, cAMP Sensor, ca2+ Sensor, and Voltage-Dependent ca2+ Channel in Insulin Granule Exocytosis", J. Biol. Chem. (2004), vol. 279:9, pp. 7956-7961.
Sinclair, M. L., et al., "Specific Expression of Soluble Adenylyl Cyclase in Male Germ Cells", Mol. Reprod. Dev. (2000), vol. 56:6-11.
Singh, L. P. et al., "Hexosamine-Induced Fibronectin Protein Synthesis in Mesangial Cells is Associated With Increases in cAMP Responsive Element Binding (CREB) Phosphorylation and Nuclear Creb: The Involvement of Protein Kinases A and C", Diabetes (2001), vol. 50, pp. 2355-2362.
Sun, X. C., et al., "HC03-Dependent Soluble Adenylyl Cyclase Activates Cystic Fibrosis Transmembrane Conductance Regulator in Corneal Endothelium", Am J Physiol Cell Physiol (2003), vol. 284, pp. C1114-C1122 (2003).
Trager, W. et al., "Human Malaria Parasites in Continuous Culture", Science, (1976), vol. 193:4254, pp. 673-675.
Trümper, A., et al., "Mechanisms of Mitogenic and Anti-Apoptotic Signaling by Glucose-Dependent Insulinotropic Polypeptide 20 in Beta(INS-1)-Cells", J. Endocrinol. (2002), vol. 174, pp. 233-246.
Turner, B. J., et al., "Effect of p75 Neurotrophin Receptor Antagonist on Disease Progression in Transgenic Amyotrophic Lateral Sclerosis Mice." J. Neurosci. Res. (2004), vol. 78, pp. 193-199.
Vossler, M. R., et al., "CAMP Activates MAP Kinase and Elk-1 Through a B-Raf and Rapl -Dependent Pathway", Cell, (1997), vol. 89:1, pp. 73-82.
Wuttke, M. S., et al., "Bicarbonate-Regulated Soluble Adenylyl Cyclase", JOP (2001), vol. 2:4, pp. 154-158.
Yan, S. et al., "Construction of Soluble Adenylyl Cyclase From Human Membrane-Bound Type 7 Adenylyl Cyclase", Methods Enzymol. (2002), vol. 345, pp. 231-241.
Yang, J., et al., "A-Kinase Anchoring Protein 100 (AKAPI 00) is localized in Multiple Subcellular Compartments in the Adult Rat Heart", J. Cell Biol. (1998), vol. 142:2, pp. 511-522.
Zaccolo, M., et al., "Discrete Microdomains With High Concentration of cAMP in Stimulated Rat Neonatal Cardiac Myocytes", Science (2002), vol. 295, pp. 1711-1715.
Zhang, Q. et al., "Nuclear Localization of Type I1 CAMP-Dependent Protein Kinase During Limb Cartilage Differentiation is Associated With a Novel Developmentally Regulated A-Kinase Anchoring Protein", Dev. Biol. (1996), vol. 176, pp. 51-61.
Zippin, J. H., et al., "C0(2)/HC0(3)(−)-Responsive Soluble Adenylyl Cyclase as a Putative Metabolic Sensor", Trends Endocrinol. Metab. (2001), vol. 12:8, pp. 366-370.
Zippin, J. H., et al., "Compartmentalization of Bicarbonate-Sensitive Adenylyl Cyclase in Distinct Signaling Microdomains", FASEB J. (2003), vol. 17, pp. 82-84.
Zippin, J. H., et al., "Bicarbonate-Responsive "Soluble" Adenylyl Cyclase Defines a Nuclear cAMP Microdomain", J. Cell Biol. (2004), vol. 164:4, pp. 527-534.
Alto, N. et al., "Intracellular Targeting of Protein Kinases and Phosphatases", Diabetes (2002), vol. 51:3, pp. S385-S388.
Ammala, C. et al., "Calcium-Independent Potentiation of Insulin Release by Cyclic AMP in Single Beta-Cells", Nature, (1993), vol. 363, pp. 356-358.
Antinozzi, P. A. et al., "Mitochondrial Metabolism Sets the Maximal Limit of Fuel-Stimulated Insulin Secretion in a Model Pancreatic Beta Cell: A Survey of Four Fuel Secretagogues", J. Biol. Chem. (2002), vol. 277:14, pp. 11746-11755.
Bacskai, B. J. et al., "Spatially Resolved Dynamics of Camp and Protein Kinase A Subunits in Aplysia Sensory Neurons", Science (1993), vol. 260, pp. 222-226.

Bailey, C. H. et al., "Toward a Molecular Definition of Long-Term Memory Storage", Proc. Natl. Acad. Sci. USA (1996), vol. 93, pp. 13445-13452.
Bevensee, M. O. et al., "Control of Intracellular pH", in Seldin, eds., The Kidney, vol. I., Lippincott Williams &Wilkins, Philadelphia, PA. (2000), pp. 391-442.
Braun, T. "Inhibition of the Soluble Form of Testis Adenylate Cyclase by Catechol Estrogens and Other Catechols", Proc. Soc. Exp. Biol. Med. (1990), vol. 194, pp. 58-63.
Buck, J. et al., "Cytosolic Adenylyl Cyclase Defines a Unique Signaling Molecule in Mammals", Proc. Natl. Acad. Sci. USA (1999), vol. 96, pp. 79-84.
Bundey, R. A., et al., "Discrete Intracellular Signaling Domains of Soluble Adenylyl Cyclase: Camps of CAMP?", Sci. STKE (2004), vol. 231, pe19, pp. 1-3.
Byus, C. V., et al., "Direct Cytochemical Localization of Catalytic Subunits Dissociated from CAMP-30 Dependent Protein Kinase in Reuber H-35 Hepatoma Cells. 11. Temporal and Spatial Kinetics", J. Cell Biol. (1982). vol. 93, pp. 727-734.
Cann, M. J., et al., "A Defined Subset of Adenylyl Cyclases is Regulated by Bicarbonate Ion", J. Biol. Chem. (2003), vol. 278:37, pp. 35033-35038.
Charles, M. A., et al., "Adenosine 3'3'-Monophosphate in Pancreatic Islets: Glucose-Induced Insulin Release", Science (1973), vol. 179, pp. 569-571.
Charles, M.A., et al., "Insulin Secretion. Interrelationships of Glucose, Cyclic Adenosine 3:5-Monophosphate, and Calcium", J Biol. Chem. (1975), vol. 250:15, pp. 6134-6140.
Chen, Y. et al., "Soluble Adenylyl Cyclase as an Evolutionarily Conserved Bicarbonate Sensor", Science (2000), vol. 289, pp. 625-628.
Constantinescu, A. et al., "Ethanol-Induced Translocation of CAMP-Dependent Protein Kinase to the Nucleus. Mechanism and Functional Consequences", J. Biol. Chem. (1999), vol. 274:35, pp. 26985-26991.
Daniel, P.B. et al., "Cyclic AMP Signaling and Gene Regulation", Annu. Rev. Nutr. (1998) vol. 18, pp. 353-383.
Davare. M. A., et al., "A Beta2 Adrenergic Receptor Signaling Complex Assembled With the ca2+ Channel Cavl.2", Science (2001) vol. 293, pp. 98-101.
Decesare, D. et al., "Transcriptional Regulation by Cyclic AMP-Responsive Factors", Prog. Nucleic Acid Res. Mol. Biol. (2000), vol. 64, pp. 343-369.
Delmeire, D., et al., "Type VIII Adenylyl Cyclase in Rat Beta Cells: Coincidence Signal DetectorlGenerator for Glucose and GLP-1", Diabetologia (2003), vol. 46, pp. 1383-1393.
Dichter, M. A. et al., "Nerve Growth Factor-Induced Increase in Electrical Excitability and Acetylcholine Sensitivity of a Rat Pheochromocytoma Cell Line", Nature (1977), vol. 268, pp. 501-504.
Dubus, P., et al., "Expression of Trk Isoforms in Brain Regions and in the Striatum of Patients With Alzheimer's Disease", Exp. Neurol. (2000), vol. 165, pp. 285-294.
Espositio, G., et al., "Mice Deficient for Soluble Adenylyl Cyclase Are Infertile Because of a Severe Sperm-Motility Defect", Proc. Natl. Acad. Sci. USA (2004), vol. 101: 9, pp. 2993-2998.
Fujimoto, K., et al., "Piccolo, A ca2+ Sensorin Pancreatic Beta-Cells. Involvement of CAMP-GEFII.Rim2.Piccolo Complex in CAMP-Dependent Exocytosis", J. Biol. Chem. (2002), vol. 277:52, pp. 50497-50502.
Gille, A., et al., "Differential Inhibition of Adenylyl Cyclase Isoforms and Soluble Guanylyl Cyclase by Purine and Pyrimidine Nucleotides", J. Biol. Chem. (2004), vol. 279:19, pp. 19955-19969.
Griffioen, G., et al., "Nutritional Control of Nucleocytoplasmic Localization of CAMP-Dependent Protein Kinase Catalytic and Regulatory Subunits in *Sacchavomyces cerevisiae*", J. Biol. Chem. (2000), vol. 275:2, pp. 1449-1456.
Hagiwara, M., et al., "Transcriptional Attenuation Following CAMP Induction Requires PP-1-Mediated Dephosphorylation of CREB", Cell (1992), vol. 70, pp. 105-113.

(56) References Cited

OTHER PUBLICATIONS

Hagiwara, M., et al., "Coupling of Hormonal Stimulation and Transcription Via the Cyclic AMP-Responsive Factor 10 CREB is Rate Limited by Nuclear Entry of Protein Kinase A", Mol. Cell. Biol. (1993), vol. 13:8, pp. 4852-4859.

Hanoune, J., et al., "Regulation and Role of Adenylyl Cyclase Isoforms", Annu. Rev. Pharmacol. Toxicol. (2001), vol. 41, pp. 145-174.

Heidemann, S. R., et al., "Synergistic Effects of Cyclic AMP and NGF on Neurite Outgrowth and MT Stability of PC 12 Cells", J. Cell Biol. (1985), vol. 100, pp. 916-927.

Holz, G. G., "EPAC: A New CAMP-Binding Protein in Support of Glucagon-Like Peptide-1 Receptor-Mediated Signal Transduction in the Pancreatic Beta-Cell", Diabetes (2004), vol. 53, pp. 5-13.

Jaiswal, B. S., et al., "Calcium Regulation of the Soluble Adenylyl Cyclase Expressed in Mammalian Spermatozoa", Proc. Natl. Acad. Sci. USA (2003), vol. 100:19, pp. 10676-10681.

Johnson, A., et al., "A Di-Leucine Sequence and a Cluster of Acidic Amino Acids are Required for Dynamic Retention in the Endosomal Recycling Compartment of Fibroblasts", Mol. Biol. Cell (2001), vol. 12, pp. 367-381.

Johnson, R. A., et al., "Isozyme-Dependent Sensitivity of Adenylyl Cyclases to P-site-Mediated Inhibition by Adenine Nucleosides and Nucleoside 3'-Polyphosphates", J. Biol. Chem. (1997), vol. 272:14, pp. 8962-8966.

Jungmann, R. A., et al., "Using Immunocolloidal Gold Electron Microscopy to Investigate CAMP-Dependent Protein Kinase Cellular Compartmentalization", Methods Enzyrnol. (1988), vol. 159, pp. 225-235.

Kang, G., et al., "EPAC-Selective cAMP Analog 8-pCPT-2'-0-Me-5 cAMP as a Stimulus for ca2+-Induced ca2+ Release and Exocytosis in Pancreatic Beta-Cells", J. Biol. Chem. (2003), vol. 278:10, pp. 8279-8285.

Kuettel et al., "Localization of Nuclear Subunits of Cyclic AMP-Dependent Protein Kinase by the Immunocolloidal Gold Method", J. Cell Biol. (1985), vol. 101, pp. 965-975.

Lacy, P. E., et al., "Method for the Isolation of Intact Islets of Langerhans From the Rat Pancreas", Diabetes (1967), vol. 16:1, pp. 35-39.

Litvin, T. N., et al., "Kinetic Properties of 'Soluble' Adenylyl Cyclase. Synergism Between Calcium and Bicarbonate", J. Biol. Chem. (2003), vol. 278:18, pp. 15922-15926.

Ma, Y. H., et al., "Constitutively Active Stirnulatory G-Protein Alpha S in Beta-Cells of Transgenic Mice Causes Counterregulation of the Increased Adenosine 3',5'-Monophosphate and Insulin Secretion", Endocrinology (1994), vol. 134:1, pp. 42-47.

Merglen, A., et al., "Glucose Sensitivity and Metabolism-Secretion Coupling Studied During Two-Year Continuous Culture in INS-1E Insulinoma Cells", Endocrinology (2004), vol. 145:2, pp. 667-678.

Michel, J. J. C., et al., "AKAP Mediated Signal Transduction", Annu. Rev. Pharmacol. Toxicol. (2002), vol. 42, pp. 235-257.

Mongillo, M., et al., "Fluorescence resonance Energy Transfer-Based Analysis of cAMP Dynamics in Live Neonatal Rat Cardiac 25 Myocytes Reveals Distinct Functions of Compartmentalized Phosphodiesterases", Cir Res (2004), vol. 95, pp. 65-75.

Muhia, D. K., et al., "Multiple Splice Variants Encode a Novel Adenylyl Cyclase of Possible Plastid Origin Expressed in the Sexual Stage of the Malaria Parasite Plasmodium falciparum", J. Biol. Chem. (2003), vol. 278:24, pp. 22014-22022.

Murray, S. A., et al., "Intracellular Kinetics of Free Catalytic Units Dissociated From Adenosine 3',5'-Monophosphate-Dependent Protein Kinase in Adrenocortical Tumor Cells (Y-1)", Endocrinology (1985), vol. 116:1, pp. 364-374.

Naik, V. M., et al., "Synthesis and Characterization of Niobium(V) Complexes with Terdentate Ono Donor Hydrazones" Database accession No. 2002:331646. IN J. Chem. Sec. A: Inorganic, Bio-Inorganic, Physical Theoretical & Analytical Chemistry.

Onkol, T., et al., "Antimicrobial Activities Os Some (2-benzimidazolythio) acetohydrazide Derivatives" J. of Faculty Pharm. of Gazi Uni (1992), vol. 9:1, pp. 46-57.

Ozaki, N., et al., "CAMP-GEFII is a Direct Target of cAMP in Regulated Exocytosis", Nat. Cell. Biol. (2000), vol. 2, pp. 805-811.

Parkkila A., et al., "Expression of Carbonic Anhydrase V in Pancreatic Beta Cells Suggests Role for Mitochondrial Carbonic Anhydrase in Insulin Secretion", J. Biol. Chem. (1998), vol. 273:38, pp. 24620-24623.

Pastor-Soler, N., et al., "Bicarbonate-Regulated 25 Adenylyl Cyclase (SAC) is a Sensor That Regulates pH-Dependent V-ATPase Recycling", Am. Soc. BioChem. Mol. Bio. (2003), vol. 278, pp. 49523-49529.

Pitt, G. S., et al., "Structurally Distinct and Stage-Specific Adenylyl Cyclase Genes Play Different Roles in Dictyostelium Development", Cell (1992), vol. 69, pp. 305-315.

* cited by examiner

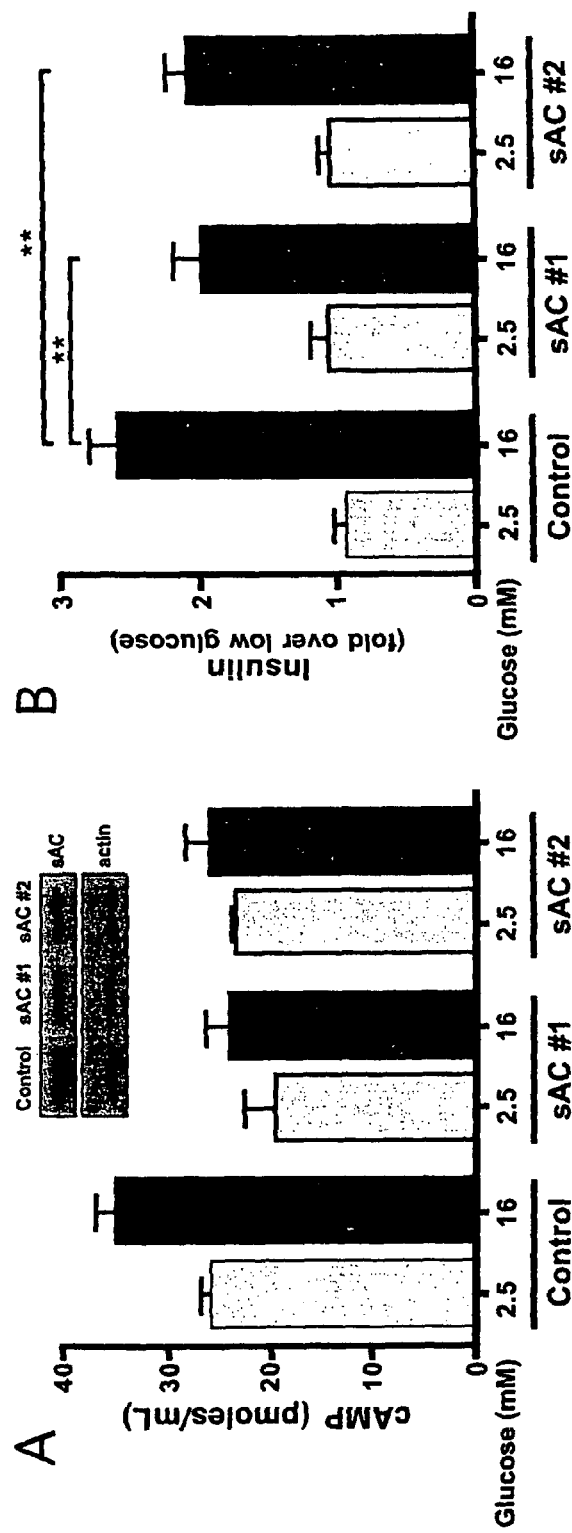
Figures 12 A-B

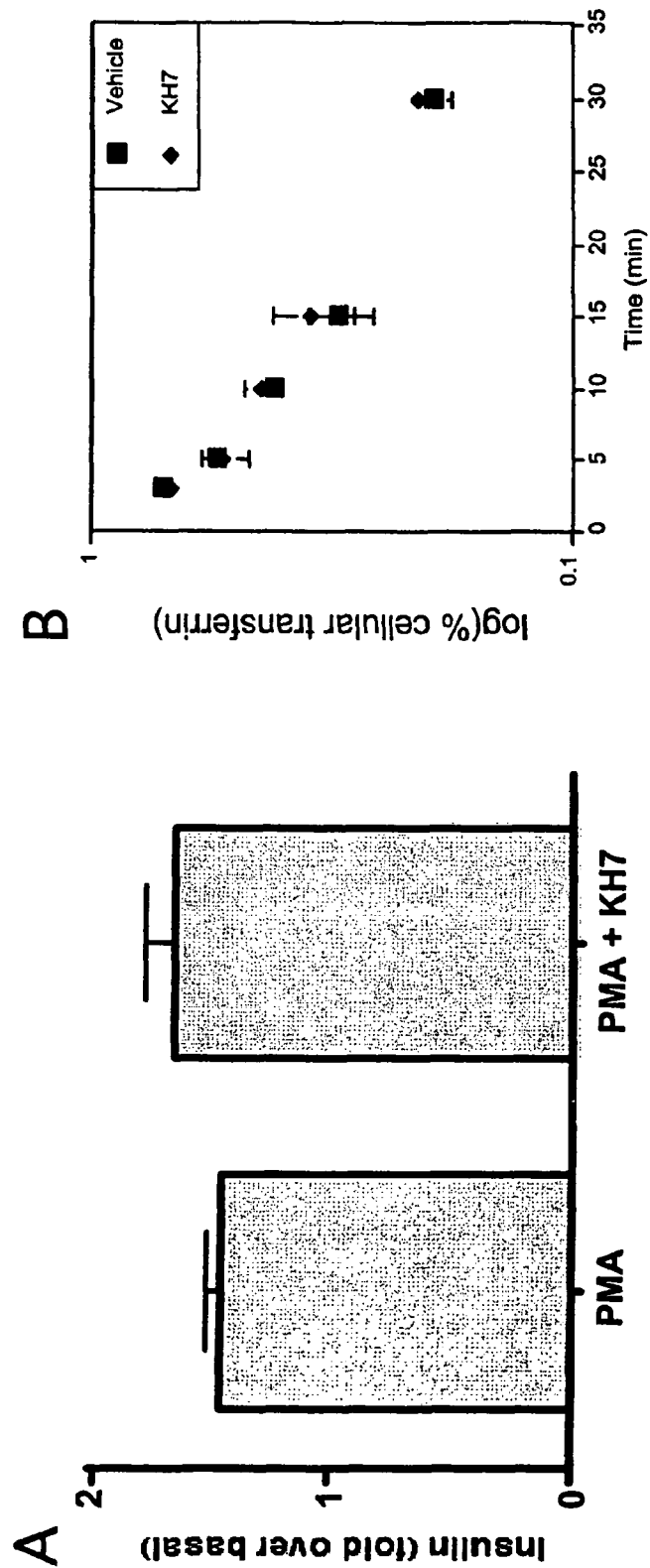
Figures 13 A-B

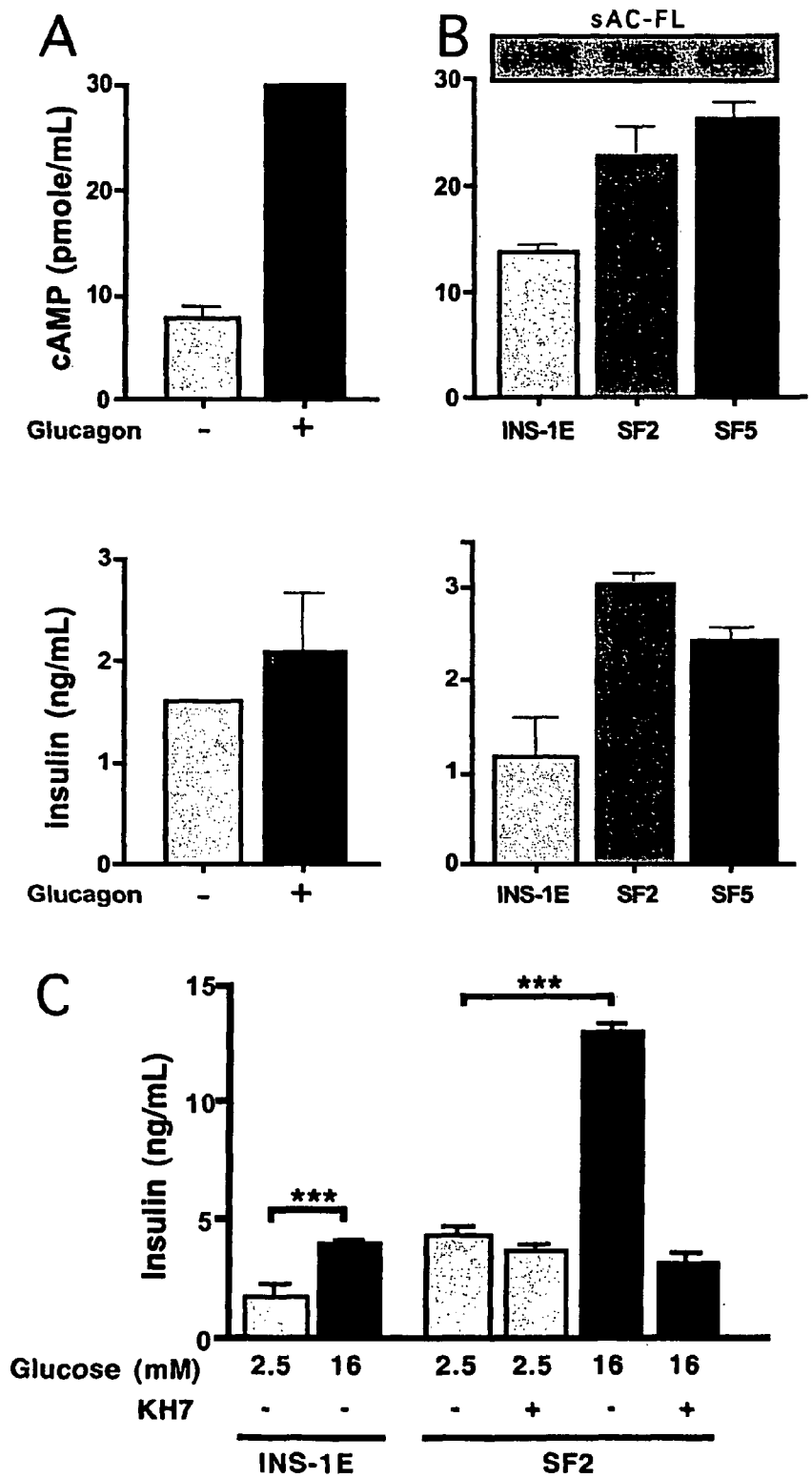
Figures 14 A-C

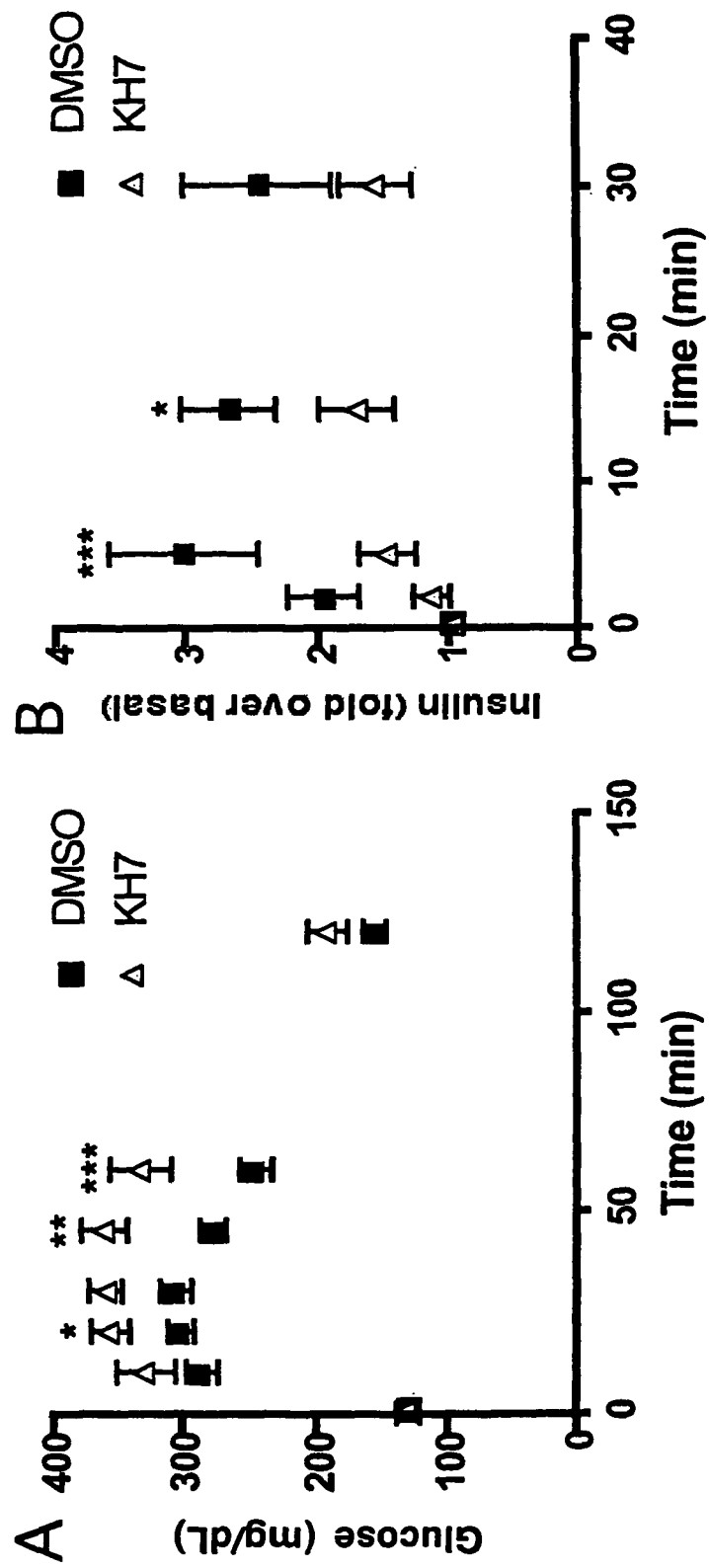
Figures 15 A-B

A 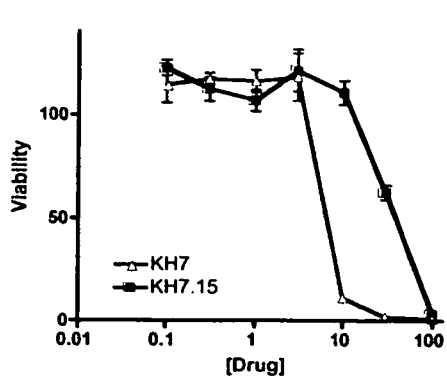
B 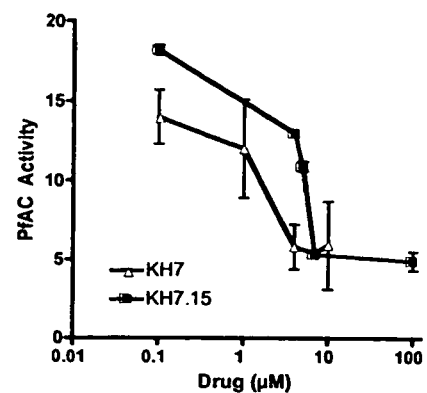
Figures 16 A-B

CHEMICAL INHIBITORS OF SOLUBLE ADENYLYL CYCLASE (SAC)

This application is the 371 national stage of PCT International Application No. PCT/US2005/001807, filed 20 Jan. 2005 and designating the United States of America, which claims the benefit of U.S. Provisional Application No. 60/537,864, filed Jan. 21, 2004, which is hereby incorporated by reference.

This invention was made with government support under Grant Nos. GM62328, HD42060, and HD38722 awarded by the National Institutes of Health. The government has certain rights in the invention.

FIELD OF THE INVENTION

The present invention relates to methods of treating a disorder mediated by soluble adenylyl cyclase in a subject by modulating soluble adenylyl cyclase in the subject, as well as methods of treating a disorder mediated by soluble adenylyl cyclase in a subject by administering to a subject an effective amount of a compound that modulates soluble adenylyl cyclase in the subject. The present invention also relates to methods of modulating soluble adenylyl cyclase by contacting eukaryotic cells with a compound that modulates soluble adenylyl cyclase.

BACKGROUND OF THE INVENTION cAMP is a nearly ubiquitous second messenger molecule that affects a multitude of cellular functions. In mammalian cells, two classes of adenylyl cyclase generate cAMP. Transmembrane adenylyl cyclases (tmACs) are tethered to the plasma membrane and regulated by heterotrimeric G proteins in response to hormonal stimuli (for review, see Hanoune et al., "Regulation and Role of Adenylyl Cyclase Isoforms," *Annu. Rev. Pharmacol. Toxicol.* 41:145-174 (2001)). A second source of cAMP, the more recently described "soluble" adenylyl cyclase (sAC), resides in discrete compartments throughout the cell (Zippin et al., "Compartmentalization of Bicarbonate-Sensitive Adenylyl Cyclase in Distinct Signaling Microdomains," *FASEB J.* 17:82-84 (2003)) and is regulated by the intracellular signaling molecules, bicarbonate (Chen et al., "Soluble Adenylyl Cyclase as an Evolutionarily Conserved Bicarbonate Sensor," *Science* 289:625-628 (2000)) and calcium (Jaiswal et al., "Calcium Regulation of the Soluble Adenylyl Cyclase Expressed in Mammalian Spermatozoa," *Proc. Natl. Acad. Sci. USA* 100:10676-10681 (2003); Litvin et al., "Kinetic Properties of 'Soluble' Adenylyl Cyclase. Synergism Between Calcium and Bicarbonate," *J. Biol. Chem.* 278: 15922-15926 (2003)).

cAMP elicits its cellular effects by activation of three known classes of effector proteins: exchange proteins activated by cAMP (EPAC), cyclic nucleotide gated ion channels, and protein kinase A (PKA). A subset of these targets resides at the plasma membrane, where they exist in macromolecular signaling complexes that also include a G protein coupled receptor, its transducing G protein, and the source of cAMP, a tmAC isoform (Davare et al., "A Beta2 Adrenergic Receptor Signaling Complex Assembled With the $Ca^{2+}$ Channel Cav1.2," *Science* 293:98-101 (2001)). The cAMP generated by tmACs appears to act locally (Rich et al., "Cyclic Nucleotide-Gated Channels Colocalize With Adenylyl Cyclase in Regions of Restricted cAMP Diffusion," *J. Gen. Physiol.* 116:147-161 (2000); Rich et al., "A Uniform Extracellular Stimulus Triggers Distinct cAMP Signals in Different Compartments of a Simple Cell," *Proc. Natl. Acad. Sci. USA* 98:13049-13054 (2001); Zaccolo et al., "Discrete Microdomains With High Concentration of cAMP in Stimulated Rat Neonatal Cardiac Myocytes," *Science* 295:1711-1715 (2002)), most likely restricted by phosphodiesterase "firewalls" (Zaccolo et al., "Discrete Microdomains With High Concentration of cAMP in Stimulated Rat Neonatal Cardiac Myocytes," *Science* 295:1711-1715 (2002); Mongillo et al., "Fluorescence resonance Energy Transfer-Based Analysis of cAMP Dynamics in Live Neonatal Rat Cardiac Myocytes Reveals Distinct Functions of Compartmentalized Phosphodiesterases," *Cir Res* 95(1):65-75 (2004)), which define the limits of these cAMP signaling microdomains. However, targets of cAMP do not solely reside at the plasma membrane. EPAC is localized to the nuclear membrane and mitochondria (Qiao et al., "Cell Cycle-Dependent Subcellular Localization of Exchange Factor Directly Activated by cAMP," *J. Biol. Chem.* 277: 26581-26586 (2002)), and PKA is tethered throughout the cell by a class of proteins called AKAP (A-kinase-anchoring proteins; Michel et al., "AKAP Mediated Signal Transduction," *Annu. Rev. Pharmacol. Toxicol.* 42:235-257 (2002)). The observation that cAMP does not diffuse far from tmACs (Bacskai et al., "Spatially Resolved Dynamics of Camp and Protein Kinase A Subunits in Aplysia Sensory Neurons," *Science* 260:222-226 (1993); Zaccolo et al., "Discrete Microdomains With High Concentration of cAMP in Stimulated Rat Neonatal Cardiac Myocytes," *Science* 295:1711-1715 (2002)) reveals that there must be another source of cAMP modulating the activity of these distally localized targets.

Soluble adenylyl cyclase (sAC; Buck et al., "Cytosolic Adenylyl Cyclase Defines a Unique Signaling Molecule in Mammals," *Proc. Natl. Acad. Sci. USA* 96:79-84 (1999); U.S. Pat. No. 6,544,768 to Buck et al.; International Publication No. WO 01/85753) is widely expressed in mammalian cells (Sinclair et al., "Specific Expression of Soluble Adenylyl Cyclase in Male Germ Cells," *Mol. Reprod. Dev.* 56:6-11 (2000)). Unlike tmACs, sAC is G protein insensitive (Buck et al., "Cytosolic Adenylyl Cyclase Defines a Unique Signaling Molecule in Mammals," *Proc. Natl. Acad. Sci. USA* 96:79-84 (1999)), and among mammalian cyclases, it is uniquely responsive to intracellular levels of bicarbonate (Chen et al., "Soluble Adenylyl Cyclase as an Evolutionarily Conserved Bicarbonate Sensor," *Science* 289:625-628 (2000)). The ubiquitous presence of carbonic anhydrases ensures that the intracellular bicarbonate concentration (and sAC activity) will reflect changes in pH (Pastor-Soler et al., "Bicarbonate-Regulated Adenylyl Cyclase (sAC) is a Sensor That Regulates pH-Dependent V-ATPase Recycling," *J. Biol. Chem.* 278:49523-49529 (2003)) and/or $CO_2$. Because $CO_2$ is the end product of energy-producing metabolic processes, sAC is poised to function as a cell's intrinsic sensor of metabolic activity (Zippin et al., "CO(2)/HCO(3)(−)-Responsive Soluble Adenylyl Cyclase as a Putative Metabolic Sensor," *Trends Endocrinol. Metab.* 12:366-370 (2001)). sAC possesses no transmembrane spanning domains (Buck et al., "Cytosolic Adenylyl Cyclase Defines a Unique Signaling Molecule in Mammals," *Proc. Natl. Acad. Sci. USA* 96:79-84 (1999)) and is distributed to subcellular compartments containing cAMP targets (Zippin et al., "Compartmentalization of Bicarbonate-Sensitive Adenylyl Cyclase in Distinct Signaling Microdomains," *FASEB J.* 17:82-84 (2003)) that are distant from the plasma membrane. sAC was also found localized inside the mammalian cell nucleus (Zippin et al., "Compartmentalization of Bicarbonate-Sensitive Adenylyl Cyclase in Distinct Signaling Microdomains," *FASEB J.* 17:82-84 (2003)).

Although cAMP has been well known as a ubiquitous second messenger molecule affecting many different cellular functions, the source of cAMP in certain cellular processes and its connection to those processes have remained undefined.

The present invention is directed to overcoming these and other deficiencies in the art.

SUMMARY OF THE INVENTION

The present invention relates to a method of treating a disorder mediated by soluble adenylyl cyclase in a subject. The method involves administering to a subject an effective amount of a compound that modulates soluble adenylyl cyclase, where the compound has the following formula:

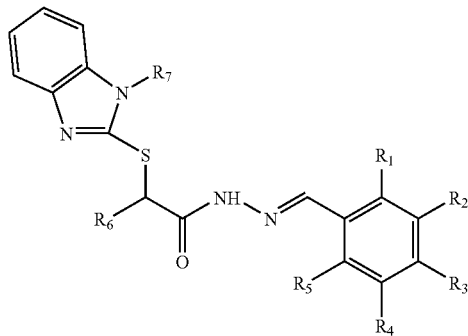

where:
$R_1$ is H, OH, alkyloxy, or halogen;
$R_2$ and $R_5$ are H or halogen;
$R_3$ is H or OH;
$R_4$ is H, alkyloxy, or halogen;
$R_6$ is H or alkyl; and
$R_7$ is H or $CH_2R_8$, where $R_8$ is H, alkyl, or substituted or unsubstituted phenyl,
with the proviso that at least one of $R_1$, $R_2$, $R_3$, and $R_4$ is a halogen,
under conditions effective to treat the disorder mediated by soluble adenylyl cyclase.

The present invention also relates to a method of treating a disorder mediated by soluble adenylyl cyclase in a subject, where the disorder is selected from the group consisting of: learning or memory disorders, malaria, fungal infection, spinal cord injury, Alzheimer's disease, amyotrophic lateral sclerosis, and peripheral neuropathy. The method involves modulating soluble adenylyl cyclase in the subject.

Another aspect of the present invention relates to a method of modulating soluble adenylyl cyclase. The method involves contacting eukaryotic cells with a compound that modulates soluble adenylyl cyclase, where the compound has the following formula:

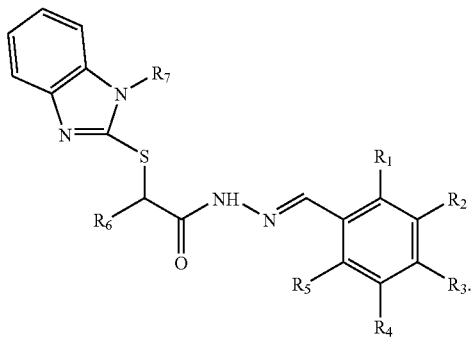

where:
$R_1$ is H, OH, alkyloxy, or halogen;
$R_2$ and $R_5$ are H or halogen;
$R_3$ is H or OH;
$R_4$ is H, alkyloxy, or halogen;
$R_6$ is H or alkyl; and
$R_7$ is H or $CH_2R_8$, where $R_8$ is H, alkyl, or substituted or unsubstituted phenyl,
with the proviso that at least one of $R_1$, $R_2$, $R_3$, and $R_4$ is a halogen,
under conditions effective to modulate soluble adenylyl cyclase.

In order to evaluate how sAC-generated cAMP might differ from the second messenger generated by tmACs, a prototypical cAMP-dependent pathway, PKA-dependent phosphorylation of cAMP response element binding protein (CREB; De Cesare et al., "Transcriptional Regulation by Cyclic AMP-Responsive Factors," *Prog. Nucleic Acid Res. Mol. Biol.* 64:343-369 (2000), which is hereby incorporated by reference in its entirety) was investigated. In a widely accepted signal transduction paradigm, extracellular signals (i.e., hormones and neurotransmitters) affect CREB family phosphorylation by stimulation of plasma membrane-bound tmACs. The generated cAMP activates nearby PKA, and the liberated catalytic subunit then appears to translocate through the cytoplasm to phosphorylate and activate CREB proteins residing inside the nucleus (Riabowol et al., "Microinjection of the Catalytic Subunit of cAMP-dependent Protein Kinase Induces Expression of the c-fos Gene," *Cold Spring Harb. Symp. Quant. Biol.* 53:85-90 (1988); Hagiwara et al., "Coupling of Hormonal Stimulation and Transcription Via the Cyclic AMP-Responsive Factor CREB is Rate Limited by Nuclear Entry of Protein Kinase A," *Mol. Cell. Biol.* 13:4852-4859 (1993), which are hereby incorporated by reference in their entirety). Intracellular signals, such as metabolic activity, also modulate CREB phosphorylation in a cAMP-dependent manner (Daniel et al., "Cyclic AMP Signaling and Gene Regulation," *Annu. Rev. Nutr.* 18:353-383 (1998); Singh et al., "Hexosamine-Induced Fibronectin Protein Synthesis in Mesangial Cells is Associated With Increases in cAMP Responsive Element Binding (CREB) Phosphorylation and Nuclear CREB: The Involvement of Protein Kinases A and C," *Diabetes* 50:2355-2362 (2001); Trumper et al., "Mechanisms of Mitogenic and Anti-Apoptotic Signaling by Glucose-Dependent Insulinotropic Polypeptide in Beta(INS-1)-Cells," *J. Endocrinol.* 174:233-246 (2002), which are hereby incorporated by reference in their entirety), but the mechanism has yet to be established. Localization of sAC inside the nucleus, in close proximity to the CREB family proteins, and its regulation by calcium and bicarbonate suggested that sAC might be responsible for modulating CREB activity in response to intracellular signals.

The present invention demonstrates the existence of a nuclear cAMP signaling microdomain that mediates bicarbonate-dependent activation of the transcription factor CREB. Bicarbonate activation of CREB represents an example of a mammalian cAMP-dependent pathway solely modulated by intrinsic cellular signals. This nuclear cAMP signaling cascade functions independently from the classically defined mechanisms leading to CREB activation, demonstrating that cAMP is a locally acting second messenger that can work autonomously in different compartments within a single cell.

Insulin secretion is known to be induced by various nutrient secretagogues: prototypically glucose. In beta-cells of the pancreas, glucose metabolism elicits an increase in cAMP, and substantial evidence implicates the cAMP signaling pathway is essential for glucose-induced insulin release. However, the link between cAMP and glucose metabolism remains unknown. The present invention pharmacologically and genetically identifies this link to be the bicarbonate/calcium-responsive sAC. Furthermore, the present invention shows that, unlike cAMP synthesized by G protein regulated tmACs, sAC generated cAMP is sufficient to elicit insulin release. Consistently, chemical inhibition of sAC in mice induces a diabetes-like phenotype. These results demonstrate that different sources of cAMP act independently and predict that sAC activators would represent a new class of diabetes therapeutic.

BRIEF DESCRIPTION OF THE DRAWINGS

FIG. 3A shows confocal immunocytochemistry of Huh7 cells with monoclonal RIIα (top middle) and polyclonal RIα antibody (top right). Top left, To-Pro 3. Overlay of To-Pro 3 with both RIIα and RIα (FIG. 3A; bottom left), RIIα (FIG. 3A; bottom middle), and RIα (FIG. 3A; bottom right). Secondary controls were negative. FIGS. 3B-C show confocal images of suspension HeLa cells immunostained with PKA regulatory subunit RIIα polyclonal antisera (FIG. 3B) and PKA regulatory subunit RIα mAb (FIG. 3C). In FIGS. 3B-C, arrows labeled A and B indicate suspension HeLa cytoplasm. Secondary controls were negative (insets). FIG. 3D shows confocal immunocytochemistry of Huh7 cells stained with R41 mAb against sAC.

FIG. 4A shows rat liver section stained with DAPI (top left, DNA), R52 biotinylated mAb (top middle, sAC), and polyclonal RIIα antisera (top right, RIIα); overlays of RIIα and sAC (bottom left), sAC and DAPI (bottom middle), and RIIα and DAPI (bottom right). Arrows labeled A indicate nuclei enriched for both sAC and PKA, whereas arrows labeled B indicate nuclei not enriched for either. FIG. 4B shows rat liver section stained with DAPI (top left, DNA), R21 mAb (top middle, sAC), and polyclonal P-CREB antisera (top right, P-CREB); overlays of P-CREB and sAC (bottom left), sAC and DAPI (bottom middle), and P-CREB and DAPI (bottom right). Arrows labeled A indicate nuclei enriched for both sAC and P-CREB, whereas arrows labeled B indicate nuclei enriched for neither. Rat liver tissue immunolocalization was confirmed to be inside the nucleus by confocal microscopy.

FIG. 5A shows Western blots of cell equivalents from HeLa whole cells (WC), low speed supernatant (S1), and nuclear-enriched high speed pellet (P2) probed with antibodies against NaK ATPase (NaK), histone H1 (Histone), cytochrome oxidase subunit III (COX), and β-tubulin (Tubulin). FIG. 5B shows immunocytochemistry of nuclei isolated from HeLa cells (P2 pellet) using CREB polyclonal antisera (FIG. 5B; CREB) and sAC R52 biotinylated mAb (FIG. 5B; sAC). Differential interference contrast microscopy (FIG. 5B; DIC) and 4'-6-Diamidino-2-phenylindole (FIG. 5B; DAPI) images shown. Bar, 10 μm. Nuclei isolated from HeLa cells (P2 pellet) immunostained with polyclonal antisera (FIG. 5C; Polyclonal) and mAb (FIG. 5C; Monoclonal) directed against both RIα and RIIα indicated that both proteins maintained their nucleoplasmic architecture throughout the fractionation procedure. Bottom row in FIG. 5C represents staining with goat anti-rabbit (middle) or goat anti-mouse controls (right) alone. Left column in FIG. 5C represents DAPI images (FIG. 5C; DAPI). Bars, 10 µm. FIG. 5D shows a Western blot of nuclear enriched P2 for sAC with R21 mAb. FIG. 5E shows Western blots of nuclear enriched P2 pellet with monoclonal (mRIα) and polyclonal (pRIα) antisera against RIα and with monoclonal (mRIIα) and polyclonal (pRIIα) antisera against RIIα. All Westerns blots resolved only single bands of the predicted molecular mass.

FIG. 6A (bottom right) highlights representative nuclei considered positive for CREB phosphorylation for quantitation. Three microscopic fields per condition were photographed and counted by a blinded scientist (FIG. 6B). Values graphed in FIG. 6B represent the percentage of positive nuclei normalized to Basal (control) averaged from five separate experiments. Ratios above each bar in FIG. 6B represent the total number of positive nuclei divided by the total number of nuclei counted for all five experiments. FIG. 6C shows a Western blot using phospho-CREB-specific antisera against equal aliquots of nuclei-enriched P2 treated with $Mg^{2+}$-ATP alone (Basal) or substrate in the presence of 1 mM 8-Br cAMP (cAMP), 40 mM bicarbonate, or 40 mM bicarbonate in the presence of either 10 µM H-89 or 1 mM 8-Br-RpcAMPs. Each band was quantitated and normalized to basal; the relative intensities are basal (1 U), cAMP (30 U), bicarbonate alone (−; 27 U), bicarbonate plus H-89 (13 U), and bicarbonate plus Rp-cAMPs (8 U). FIG. 6D shows a Western blot using phospho-CREB-specific antisera against equal aliquots of nuclei-enriched P2 treated with 10 µM forskolin (FSK) or with 40 mM of bicarbonate alone (+HCO$_3$) or in the presence of 50 µM of a sAC specific inhibitor, KH7 (+HCO$_3$+KH7).

FIG. 7A shows a rat pancreatic islet immunostained with biotinylated anti-sAC monoclonal antibody R52b (left) and anti-insulin (middle) with overlay (right). FIG. 7B shows a betaTC6 insulinoma cell (DIC image, first image from left) stained with anti-C-term sAC polyclonal (second image from left), anti-insulin (third image from left), and overlay (fourth image from left). FIG. 7C shows RINm5F insulinoma cells (DIC image, first image from left) stained with anti-C-term sAC polyclonal (second image from left), anti-insulin (third image from left), and overlay (fourth image from left). FIG. 7D shows an INS-1E insulinoma cell stained with DAPI (first image from left), anti-sAC biotinylated monoclonal antibody R52b (second image from left), anti-insulin (third image from left), and overlay (fourth image from left). Scale bars indicated.

FIG. 8A shows bicarbonate/calcium stimulated pure sAC protein in the presence of indicated concentrations of the P site inhibitor, 2'5'ddAdo (µM). FIG. 8B shows 15 minute cAMP accumulation in intact INS-1E cells in the absence of any stimulator (Basal, white bar) or in the presence of 10 µM Forskolin in the absence (Forskolin, lightly shaded bar) or presence (Forskolin+P site, darkly shaded bar) of 50 µM 2'5'ddAdo. FIG. 8C shows adenylyl cyclase activity in INS-1E cell lysate in the absence of any stimulator (Basal, white bar) or in the presence of 10 µM Forskolin in the absence (Forskolin, lightly shaded bar) or presence (Forskolin+P site, darkly shaded bar) of 50 µM 2'5'ddAdo.

FIG. 10A shows GSIS (measured over 30 minutes) in the presence of 2.5 mM glucose (light square) or 16 mM glucose (dark squares) with indicated concentrations of KH7 (µM). Shown is a representative figure performed at least three times; values represent averages of duplicate determinations±standard deviation (SD). Insulin secreted (FIG. 10B) and intracellular cAMP levels (FIG. 10C) were determined from the same wells (n=6) incubated in low glucose (2.5 mM, light bars) or high glucose (16 mM, dark bars) in the presence of vehicle (−), 30 µM KH7 (7), 30 µM KH7.15 (7.15), 50 µM 2-hydroxyestradiol (2OH), or 50 µM 2'5'ddAdo (Psite). Values represent mean A standard error of the mean (SEM). ANOVA analysis was performed with asterisks indicating statistical significance as compared to the relevant vehicle control values, except where otherwise noted by a bar above the graph. FIG. 10D shows GSIS (i.e., insulin released in the presence of 16 mM glucose) from INS-1E cells over 15 minutes in the presence of vehicle (DMSO), 30 µM K17 (KH7), or 50 µM 2'5'ddAdo (Psite) with ("+", dark bars) or without ("−", light bars) 0.5 mM IBMX. Values represent mean±SEM (n=4). ANOVA analysis was performed, with asterisks indicating statistical significance as compared to vehicle control value (−IBMX). FIG. 10E shows insulin secreted over 15 minutes in the presence of 2.5 mM (light bar) or 16 mM glucose (dark bars) in the presence of 50 µM KH7 (KH7) or KH7 and 1 mM 8-Br-SpcAMP (KH7+cAMP). Shown is a representative figure repeated multiple times; values are averages from duplicate determinations±SD. FIG. 10F shows insulin released from mouse islets cultured in low glucose (2.8 mM, light bars) or high glucose (16.7 mM, dark bars) for 30 minutes in the presence of vehicle (DMSO), 30 µM KH7 (KH7), or 30 µM KH7.15 (KH7.15). Values represent mean±SEM (n=3). ANOVA analysis was performed, with asterisks indicating statistically significant differences. For all graphs, *=p<0.05; =p<0.0; *=p<0.001; and ns=no statistically significant difference.

FIGS. 12A-B show that sAC-specific RNAi blunts glucose-induced cAMP generation and insulin release. FIG. 12A shows intracellular cAMP generated in low (2.5 mM, light bars) or high glucose (16 mM, dark bars) in INS-1E cells transfected with negative control RNAi oligos (control) or two different RNAi oligonucleotides directed against sAC (sAC #1 and sAC #2). Shown is a representative figure; values represent duplicate transfected wells. Inset shows representative Western blots of INS-1E cells transfected with the indicated RNAi oligonucleotides using anti-sAC (monoclonal antibody R21) or anti-β actin antibody. FIG. 12B shows insulin released (over 30 minutes) in low glucose (2.5 mM, light bars) or high glucose (16 mM, dark bars) from cells transfected with the indicated RNAi oligonucleotides. Shown is the average fold insulin released in high glucose relative to insulin released in low glucose from eight (8) independently transfected wells. To facilitate comparisons between transfections, all data were first normalized to the average insulin released in low glucose from the combined control transfected wells. Values represent mean±SEM (n=8). ANOVA analysis was performed with asterisks indicating statistically significant differences. **=p<0.01.

FIGS. 13A-B demonstrate that K17 does not affect PMA induced insulin release or transferrin recycling in INS-1E cells. FIG. 13A shows PMA (300 nM) stimulated insulin release (2.5 mM glucose) for 30 minutes in the presence of DMSO or KH7 (30 µM). Values are mean±SEM (n=3). Data represents fold insulin released over insulin released in low glucose (basal). FIG. 13B shows transferrin recycling over 30 minutes in the presence of DMSO (squares) or KH7 (30 µM; diamonds). Shown is a representative experiment repeated at least three times. Data points represent averages of duplicate determinations with error bars indicating standard deviation.

FIGS. 14A-C illustrate that sAC-generated cAMP, distinct from tmAC-generated cAMP, is sufficient to elicit insulin secretion. FIG. 14A shows cAMP accumulation (top) and insulin secretion (bottom) over 15 minutes in INS-1E cells in low glucose (2.5 mM) alone (lightly shaded bars) or after stimulation with 10 nM glucagon (darkly shaded bars). Shown is a representative assay repeated at least five times; values indicate duplicate determinations with standard deviations. FIG. 14B shows cAMP accumulation (top) and insulin secretion (bottom) in 2.5 mM glucose over 15 minutes in INS-1E cells (open bars), SF2 cells (lightly shaded bars), or SF5 cells (darkly shaded bars). Shown is a representative assay repeated at least five times; values indicate duplicate determinations with standard deviations. Insert is a Western blot indicating the levels of sAC protein in INS-1E, SF2, and SF5 cells. FIG. 14C shows insulin secretion from INS-1E or SF2 after incubation for 15 minutes in either 2.5 mM (light bars) or 16 mM glucose (dark bars) in the presence or absence of 30 µM KH7. Values represent mean±SEM (n=3). ANOVA analysis was performed with asterisks indicating statistically significant differences. ***=p<0.001.

FIGS. 15A-B illustrate that KH7 inhibits glucose tolerance and insulin release in C57BL/6 mice. FIGS. 15A-B show serum glucose (n=8) (FIG. 15A) and insulin levels (n=5) (normalized to basal) (FIG. 15B) in mice at the indicated times, following i.p. glucose injection (1 g/kg) into animals pretreated with 100 µmoles/kg [49 mg/kg] KH7 (open triangles) or DMSO vehicle control (closed squares). Values represent mean±SEM. Repeated measures ANOVA analysis was performed with asterisks indicating statistical significance of KH7 treatment as compared to vehicle at the time point indicated. For all graphs, *=p<0.05; =p<0.01; and *=p<0.001.

FIGS. 16A-B illustrate plasmodium viability (FIG. 16A) and cyclase activity (FIG. 16B) in the presence of KH7 and KH7.15. Plasmodium cultures were incubated in the indicated concentrations of KH7 or KH7.15 for 24 hours and viability assessed by luciferase assay (FIG. 16A). Adenylyl cyclase activity in whole cell extract of isolated parasites was assayed in the presence of $MnCl_2$ and ATP and the indicated concentrations of KH7 or KH7.15 (FIG. 16B).

FIG. 17A depicts the bicarbonate activation of JR3, while FIG. 17B shows the KH7 inhibition of JR3.

DETAILED DESCRIPTION OF THE INVENTION

Figure 1:
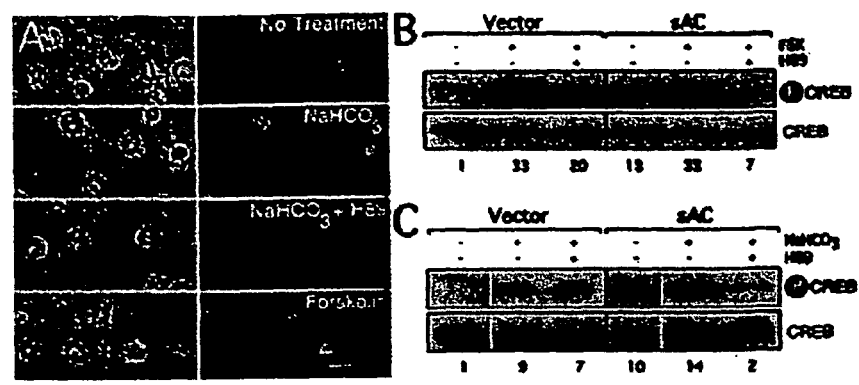
FIGS. 1A-C show that bicarbonate induces CREB phosphorylation via sAC activation in a PKA-dependent manner. COS7 cells were starved for bicarbonate for 60 min and were either incubated in the same bicarbonate starvation media for an additional 30 min (FIG. 1A; No Treatment), incubated in normal, bicarbonate-containing DME in 5% $CO_2$ for 30 min (FIG. 1A; $NaHCO_3$), or preincubated with 10 μM H89 for 10 min followed by incubation in normal, bicarbonate-containing DME in 5% $CO_2$ for 30 min (FIG. 1A; $NaHCO_3$+H89). As a control, COS7 cells grown in normal DME in 5% $CO_2$ were incubated with 10 μM of forskolin for 30 min (FIG. 1A; Forskolin). Cells were immunostained with phospho-CREB antisera (FIG. 1A, right). The images on the left in FIG. 1A are phase images of cells on the right. Bar, 50 μm. COS7 cells were transfected with vector control or a 48-kD isoform of sAC, and cells were assayed 36 h after transfection (FIG. 1B). Cells were treated with a vehicle control (DMSO) or 10 μM H89 for 10 min and stimulated with 10 μM of forskolin or given vehicle control (DMSO) for an additional 30 min (FIG. 1B). Transfected cells were starved for bicarbonate and were either incubated in the same bicarbonate starvation media for an additional 30 min; incubated in normal, bicarbonate-containing DME in 5% $CO_2$ for 30 min; or preincubated with 10 μM H89 for 10 min followed by incubation in normal, bicarbonate-containing DME in 5% $CO_2$ for 30 min (FIG. 1C). Top panels in FIGS. 1B-C show Western blots using anti-phospho-CREB antisera with phosphorylated CREB (P-CREB) protein indicated; the bottom panels show Western blots using CREB-specific antisera with total CREB protein indicated. Shown below the Western blots in FIGS. 1B-C are the intensities of phospho-CREB relative to CREB normalized to the vector control with no treatment (first lane).

The present invention relates to a method of treating a disorder mediated by soluble adenylyl cyclase in a subject. The method involves administering to a subject an effective amount of a compound that modulates soluble adenylyl cyclase, where the compound has the following formula:

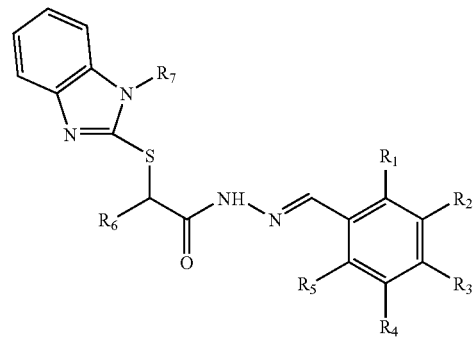

where:

$R_1$ is H, OH, alkyloxy, or halogen;

$R_2$ and $R_5$ are H or halogen;

$R_3$ is H or OH;

$R_4$ is H, alkyloxy, or halogen;

$R_6$ is H or alkyl; and $R_7$ is H or $CH_2R_8$, where $R_8$ is H, alkyl, or substituted or unsubstituted phenyl, with the proviso that at least one of $R_1$, $R_2$, $R_3$, and $R_4$ is a halogen, under conditions effective to treat the disorder mediated by soluble adenylyl cyclase. In one embodiment of the present invention, the compound inhibits soluble adenylyl cyclase. In another embodiment, the compound activates soluble adenylyl cyclase.

In another embodiment of the present invention, the compound has the following formula:

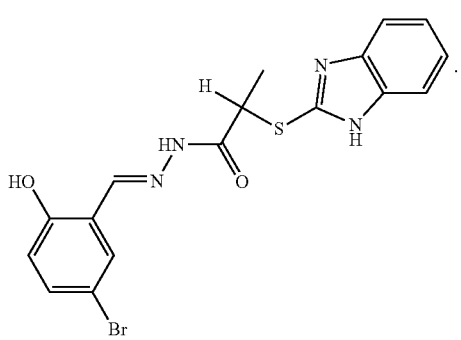

KH7

In another embodiment, the compound has the following formula:

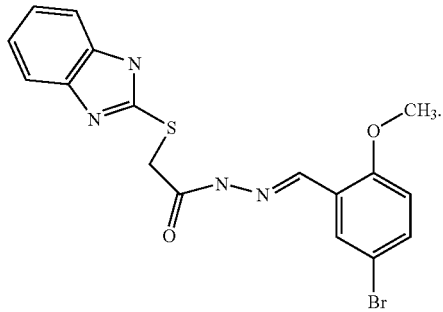

KH7.05

In another embodiment, the compound has the following formula:

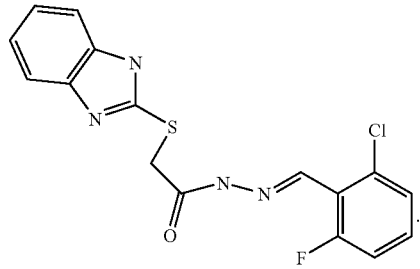

KH7.06

In another embodiment, the compound has the following formula:

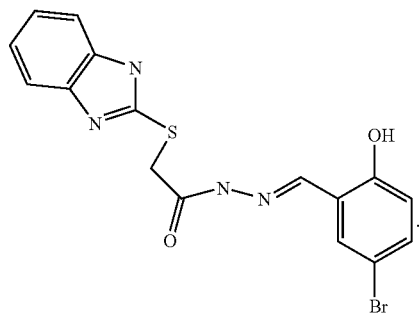

KH7.07

In another embodiment, the compound has the following formula:

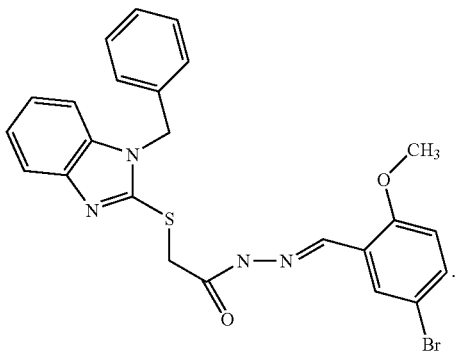

KH7.11

In another embodiment, the compound has the following formula:

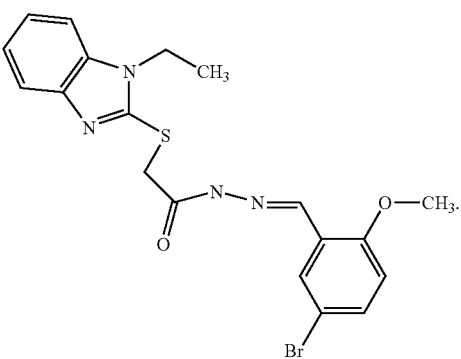

KH7.12

In another embodiment, the compound has the following formula:

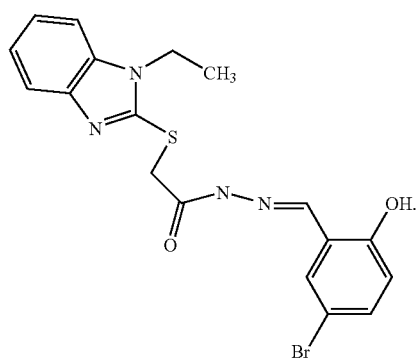

KH7.13

In yet another embodiment, the compound has the following formula:

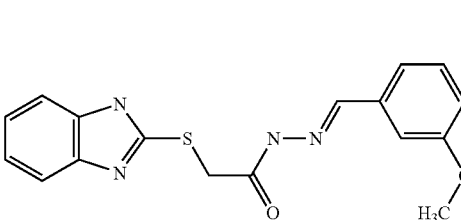

KH7.15

Suitable examples of disorders that are mediated by soluble adenylyl cyclase include, but are not limited to: learning or memory disorders, male fertility/sterility (Chen et al., "Soluble Adenylyl Cyclase as an Evolutionarily Conserved Bicarbonate Sensor," *Science* 289:625-628 (2000); Esposito et al., "Mice Deficient for Soluble Adenylyl Cyclase Are Infertile Because of a Severe Sperm-Motility Defect," *Proc. Natl. Acad. Sci. USA* 101:2993-2998 (2004), which are hereby incorporated by reference in their entirety), glaucoma (Sun et al., "$HCO_3^-$-Dependent Soluble Adenylyl Cyclase Activates Cystic Fibrosis Transmembrane Conductance Regulator in Corneal Endothelium," *Am J Physiol Cell Physiol* 284: C1114-C1122 (2003), which is hereby incorporated by reference in its entirety), metabolic acidosis/alkalosis, diabetes, metabolic disorders, breathing disorders (Sun et al., "$HCO_3^-$-Dependent Soluble Adenylyl Cyclase Activates Cystic Fibrosis Transmembrane Conductance Regulator in Corneal Endothelium," *Am J Physiol Cell Physiol* 284: C1114-C1122 (2003), which is hereby incorporated by reference in its entirety), insulin resistance, hyperinsulinemia, malaria, fungal infection, spinal cord injury, Alzheimer's disease, amyotrophic lateral sclerosis, and peripheral neuropathy.

The compounds of the present invention may be orally administered; for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the active compound. The percentage of the compound in these compositions may, of course, be varied and may conveniently be between about 2% to about 60% of the weight of the unit. The amount of active compound in such therapeutically useful compositions is such that a suitable dosage will be obtained.

The tablets, capsules, and the like may also contain a binder, such as gum tragacanth, acacia, corn starch, or gelatin; excipients, such as dicalcium phosphate; a disintegrating agent, such as corn starch, potato starch, alginic acid; a lubricant, such as magnesium stearate; and a sweetening agent, such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to the active ingredient, sucrose as a sweetening agent, methyl and propylparabens as preservatives, a dye, and flavoring, such as a cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form, such as in a nebulizer or atomizer.

The present invention also relates to a method of treating a disorder mediated by soluble adenylyl cyclase in a subject, where the disorder is selected from the group consisting of: learning or memory disorders, malaria, fungal infection, spinal cord injury, Alzheimer's disease, amyotrophic lateral sclerosis, and peripheral neuropathy. The method involves modulating soluble adenylyl cyclase in the subject.

Another aspect of the present invention relates to a method of modulating soluble adenylyl cyclase. The method involves contacting eukaryotic cells with a compound that modulates soluble adenylyl cyclase, where the compound has the following formula:

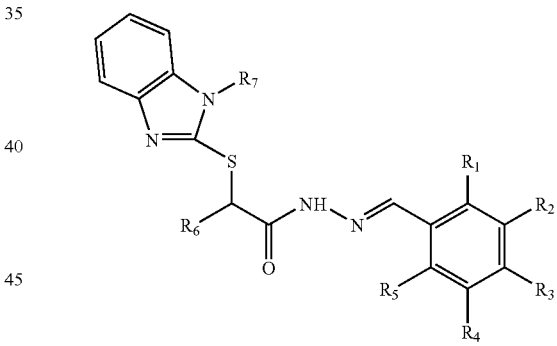

where:
$R_1$ is H, OH, alkyloxy, or halogen;
$R_2$ and $R_5$ are H or halogen;
$R_3$ is H or OH;
$R_4$ is H, alkyloxy, or halogen;
$R_6$ is H or alkyl; and
$R_7$ is H or $CH_2R_8$, where $R_8$ is H, alkyl, or substituted or unsubstituted phenyl,
with the proviso that at least one of $R_1$, $R_2$, $R_3$, and $R_4$ is a halogen,
under conditions effective to modulate soluble adenylyl cyclase.

EXAMPLES

The following examples are provided to illustrate embodiments of the present invention but are by no means intended to limit its scope.

Example 1

Cell Growth and Transfections

All cell lines were grown in DME (44 mM sodium bicarbonate) supplemented with 10% FBS. Where indicated, cells were transfected using Lipofectamine 2000 (Invitrogen, Carlsbad, Calif.) as per the manufacturer's instructions. Cells were incubated with DNA for 5 h in OPTI-MEM (Invitrogen), and then switched to normal media. Bicarbonate starvation was conducted by changing media to bicarbonate-free DME (44 mM Hepes) supplemented with 10% FBS for at least 1 h at 37° C. under ambient air conditions. Bicarbonate stimulation consisted of returning cells to normal bicarbonate-containing media and placing them in a 5% $CO_2$ incubator. For $PGE_2$ or forskolin stimulation, cells were grown in normal media under 5% $CO_2$. Stimulation was accomplished by replacing media with normal media containing 1 µM $PGE_2$ or 10 µM forskolin. For Western analysis, cells were lysed immediately by direct addition of SDS sample buffer.

Example 2

Immunocytochemistry

Cells or nuclei were washed in PBS and fixed for either 30 min in 4% PFA and permeabilized in 0.1% Triton X-100 or fixed for 15 min in 2% PFA and permeabilized in 0.05% Triton X-100. Liver from adult rat was rapidly excised, placed between two thinly sliced pieces of bovine liver, and snap frozen in isopentane cooled with liquid nitrogen. 6-µM-thick cryosections were collected on superfrost slides (Fisher Scientific, Hampton, N.H.) and stained within 1 day of sectioning. Tissue was fixed for 30 min in 4% PFA and permeabilized in 0.1% Triton X-100 for 15 min. All samples were blocked in 2% BSA for at least 1 h. Cells or tissues were stained with anti-sAC R41 or R52 biotinylated mAbs or R21 mAb (1:100) generated against human 48-kD isoform of sAC ($sAC_t$) antigen as described previously (Zippin et al., "Compartmentalization of Bicarbonate-Sensitive Adenylyl Cyclase in Distinct Signaling Microdomains," *FASEB J.* 17:82-84 (2003), which is hereby incorporated by reference in its entirety), anti-PKA regulatory subunit (RIα and RIIα) polyclonal antisera (1:100; Chemicon, Temecula, Calif., and Cedarlane Laboratories Limited, Hornby, Ontario, Canada) or mAbs (Becton Dickinson, Franklin Lakes, N.J.), and anti-CREB or anti-phospho-CREB polyclonal antisera (1:500; Cell Signaling Technologies, Beverly, Mass.) overnight in 2% BSA, 0.01% Triton X-100; washed three times for 10 min each in 2% BSA, 0.01% Triton X-100; stained for 1 h at room temperature with goat anti-rabbit Alexa Fluor 488, goat anti-mouse Alexa Fluor 568, or goat anti-mouse Alexa Fluor 594 (Molecular Probes, Eugene, Oreg.); treated with 4'-6-Diamidino-2-phenylindole (DAPI) for 5 min or To-Pro 3 (1:500; Molecular Probes) for 15 min; and washed and mounted with gelvatol/DABCO (Sigma-Aldrich, St. Louis, Mo.).

For phospho-CREB immunolocalization, cells or nuclei were fixed in 4% PFA for 30 min, permeabilized in 0.1% Triton X-100 for 15 min, blocked for at least 1 h in 3% BSA, and immunostained using phospho-CREB polyclonal antisera (1:500; Cell Signaling Technologies) overnight at 4° C. Staining was visualized by incubation with goat anti-rabbit Alexa Fluor 488 (Molecular Probes) for 1 h at room temperature, treated with DAPI for 5 min, and washed and mounted with gelvatol/DABCO (Sigma-Aldrich). Fluorescent images were recorded by a digital camera (Hamamatsu, Bridgewater, N.J.) connected to an inverted epifluorescent microscope (Nikon, Melville, N.Y.). Images were taken at the same exposure time and gain, and all photographic manipulations were performed equally. Phospho-CREB-positive nuclei were quantified in multiple fields from each stained slide by a blinded experimenter.

Confocal images were acquired with a confocal system (model LSM 510; Carl Zeiss MicroImaging, Inc., Chester, Va.). Goat anti-rabbit Alexa Fluor 488 was excited with a 488-nM Kr/Ar laser, goat anti-mouse Alexa Fluor 568 was excited with a 568-nm Kr/Ar laser, and To-Pro 3 was excited with a 633-nm Kr/Ar laser.

Example 3

Isolation of Nuclei

Nuclei were isolated by cellular lysis followed by differential centrifugation (Spector et al. (eds.), "Culture and Biochemical Analysis of Cells," in *Cells: A Laboratory Manual, Vol.* 1 Cold Spring Harbor Laboratory Press, Cold Spring Harbor, N.Y. (1998), which is hereby incorporated by reference in its entirety) through OptiPrep (Axis-Shield, Oslo, Norway). HeLa cells grown in suspension were lysed by detergent treatment in TM-2 buffer (0.01 M Tris-HCl, pH 7.4, 1.5 mM $MgCl_2$, 150 mM NaCl, 0.5 mM PMSF, 10 µg/ml apoprotin, and 10 µg/ml leupeptin) containing 100 µg/ml of digitonin followed by a 1,000-g spin. Supernatant (S1) was removed and the pellet was resuspended in 0.25 M sucrose, 25 mM KCl, 30 mM $MgCl_2$, and 20 mM Tris-HCl, pH 7.8. The resuspended pellet and 60% OptiPrep iodixanol were mixed (30% OptiPrep final) and centrifuged at 10,000 g for 20 min. The supernatant was removed and the nuclei-enriched pellet (P2) was resuspended in TM-2 buffer without detergent.

Example 4

CREB Phosphorylation and Adenylyl Cyclase Assays

Equal aliquots of nuclei-enriched P2 preparations were incubated in 50 µl of the final volume of 100 mM Tris, pH 7.2, 10 mM $MgCl_2$, and 5 mM ATP for CREB phosphorylation and 100 mM Tris, pH 7.2, 10 mM $MgCl_2$, 5 mM ATP, and 0.5 mM IBMX for adenylyl cyclase assay with the indicated additions for 10 min (CREB phosphorylation) or 15 min (adenylyl cyclase) at 37° C. Reactions were stopped by the addition of 20 µl of SDS sample buffer (CREB phosphorylation) or by being placed into a 100° C. heat block for 3 min (adenylyl cyclase).

For whole cell and isolated nuclei CREB phosphorylation assays, equal cell or nuclear equivalents were separated under reducing conditions using a 10% SDS-PAGE, transferred to a PVDF membrane, and probed for CREB (rabbit polyclonal antiserum; Chemicon, Temecula, Calif.) and phosphorylated CREB (rabbit polyclonal antiserum; Upstate Biotechnology, Temecula, Calif.). HRP-conjugated secondary antibodies were used, and bands were visualized using ECL. Image analysis software (model Fluorchem 8800; Alpha Innotech, San Leandro, Calif.) was used to quantitate Western results. Intensities of phospho-CREB bands were normalized to total CREB.

cAMP produced in the cyclase assays was detected using a competition-based assay with [$^3$H]cAMP (Amersham Biosciences, Piscataway, N.J.) and compared with a cAMP standard curve for quantitation.

Inhibitor profiles were determined by adenylyl cyclase assay (Assay Designs, Inc., Ann Arbor, Mich.) using purified sAC protein (Litvin et al., "Kinetic Properties of 'Soluble' Adenylyl Cyclase. Synergism Between Calcium and Bicarbonate," *J. Biol. Chem.* 278:15922-15926 (2003), which is hereby incorporated by reference in its entirety) in the presence of 10 mM $NaHCO_3$, 0.5 mM $CaCl_2$, 10 mM $MgCl_2$, and 10 mM ATP or a mixture of purified catalytic domains, C1 and C2, from Type VII tmAC (Yan et al., "Construction of Soluble Adenylyl Cyclase From Human Membrane-Bound Type 7 Adenylyl Cyclase," *Methods Enzymol.* 345:231-241 (2002), which is hereby incorporated by reference in its entirety) in the presence of 5 mM $MgCl_2$ and 1 mM ATP.

Example 5

Quantitation of Isolated Nuclei (P2 Fraction) Immunocytochemistry

Nuclei were treated with $Mg^{2+}$-ATP alone or in combination with bicarbonate, forskolin, or 8-Br-cAMP for 10 min, spread on a chilled slide, stored at −20° C., and immunostained using phospho-CREB-specific antisera. Nuclei were also treated with DAPI to differentiate intact nuclei from membrane ghosts. DAPI-positive nuclei were scored for phosho-CREB immunofluorescence. Nuclei with detectable staining (FIG. 6A, $NaHCO_3$) were considered positive for CREB phosphorylation, whereas nuclei with no detectable staining (FIG. 6A, Basal) were counted as negative. Multiple microscopic fields were photographed for each condition, and data was combined from three to five separate experiments.

Example 6

Western Analysis

Equal cell equivalents, unless otherwise noted, were separated under reducing conditions using a 10% SDS-PAGE, transferred to PVDF membrane, and blocked in 5% milk. The blots were probed with antibodies against either NaK ATPase (monoclonal, 1:50; Santa Cruz Biotechnology, Inc., Santa Cruz, Calif.), histone H1 (monoclonal, 1:100; Santa Cruz Biotechnology, Inc.), cytochrome oxidase subunit III (monoclonal, 2 µg/ml; Molecular Probes), β-tubulin (monoclonal, 1:1000; Sigma-Aldrich), sAC (R21 mAb, 1:500), monoclonal RIα or RIIα antibodies (1:250; Becton Dickinson), or polyclonal RIα or RIIα antisera (1:5000; Chemicon) overnight. HRP-conjugated secondary antibodies were used and bands were visualized using ECL.

Example 7

Bicarbonate Induces CREB Phosphorylation

Bicarbonate treatment of cells uniquely activates sAC (Chen et al., "Soluble Adenylyl Cyclase as an Evolutionarily Conserved Bicarbonate Sensor," *Science* 289:625-628 (2000), which is hereby incorporated by reference in its entirety), whereas activation by G proteins or forskolin only stimulates tmACs; therefore, these agents can be used to differentially stimulate the two classes of mammalian adenylyl cyclase. To determine whether sAC activation would elicit PKA activation of CREB, a well-characterized target of tmAC-generated cAMP, cells were treated with bicarbonate, and PKA-dependent phosphorylation of CREB was measured using antisera specific for the PKA (Ser133) phosphorylated form of CREB. Hormonal stimulation of CREB transcription factors, acting through tmACs, reaches its peak in 30 min (Hagiwara et al., "Transcriptional Attenuation Following cAMP Induction Requires PP-1-Mediated Dephosphorylation of CREB," *Cell* 70:105-113 (1992), which is hereby incorporated by reference in its entirety). Treatment of COS7 cells with forskolin, which will activate the total cellular pool of tmACs, stimulated nuclear immunofluorescent staining and Western blot immunoreactivity using the phosphospecific antisera (FIGS. 1A and 1B). Treatment of COS7 cells for the same amount of time (30 min) with bicarbonate also resulted in CREB phosphorylation (FIGS. 1A and 1C). These increases in phospho-CREB immunostaining were inhibited by pretreatment with H89, confirming the involvement of PKA (FIGS. 1A-C). Overexpression of sAC led to an increase in basal CREB phosphorylation (FIGS. 1B and 1C, fourth lane), suggesting that sAC-generated cAMP was sufficient to activate CREB. Consistent with its bicarbonate responsiveness (Chen et al., "Soluble Adenylyl Cyclase as an Evolutionarily Conserved Bicarbonate Sensor," *Science* 289:625-628. (2000), which is hereby incorporated by reference in its entirety), sAC overexpressing COS7 cells displayed enhanced bicarbonate-dependent CREB phosphorylation (FIG. 1C, second and fifth lanes), which was also blocked by H89 (FIG. 1C). The ability of either bicarbonate or forskolin to induce CREB phosphorylation revealed that CREB represents a downstream target of both tmAC- and sAC-generated cAMP.

Example 8

Time Course of Bicarbonate-Induced CREB Phosphorylation

Figure 2:
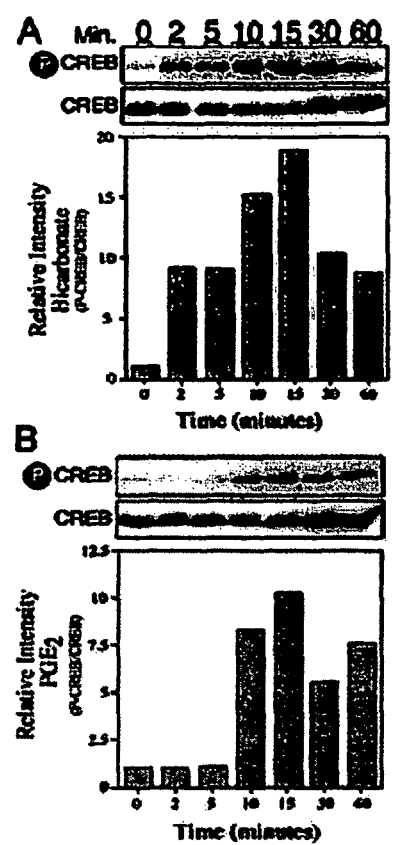
FIGS. 2A-B show the time course of CREB phosphorylation by sAC and tmAC. Huh7 cells were starved for 1 h for bicarbonate and $CO_2$ and incubated in 44 mM of normal, bicarbonate-containing DME in 5% $CO_2$ for the time indicated (FIG. 2A) or kept in normal media and treated with 1 μM $PGE_2$ for the time indicated (FIG. 2B). Top panels in FIGS. 2A-B show Western blots using anti-phospho-CREB antisera with phosphorylated CREB (P-CREB) protein indicated; the bottom panels show Western blot using CREB-specific antisera with total CREB (CREB) protein indicated. Shown below the Western blots in FIGS. 2A-B are graphical representations of the intensities of phospho-CREB relative to CREB normalized to the 0 min time point (first lane).

The time course of CREB activation in response to a hormonal activator of tmACs, $PGE_2$, was directly compared to the time course of CREB activation in response to specific sAC activator, bicarbonate, in a liver cell line (Hagiwara et al., "Transcriptional Attenuation Following cAMP Induction Requires PP-1-Mediated Dephosphorylation of CREB," *Cell* 70:105-113 (1992), which is hereby incorporated by reference in its entirety). Phosphorylation of CREB in response to bicarbonate occurred rapidly; increases in phospho-CREB were detected within 2 min, the earliest time tested (FIG. 2A). In contrast, $PGE_2$ (FIG. 2B) or forskolin stimulation of CREB phosphorylation was detectable only after 5 min, consistent with published papers (Hagiwara et al., "Transcriptional Attenuation Following cAMP Induction Requires PP-1-Mediated Dephosphorylation of CREB," *Cell* 70:105-113 (1992), which is hereby incorporated by reference in its entirety). The longer activation kinetics after PGE2 or forskolin stimulation may reflect the time required for translocation of PKA catalytic subunit into the nucleus from the plasma membrane where it is activated by a hormonally modulated tmAC (Hagiwara et al., "Coupling of Hormonal Stimulation and Transcription Via the Cyclic AMP-Responsive Factor CREB is Rate Limited by Nuclear Entry of Protein Kinase A," *Mol. Cell. Biol.* 13:4852-4859 (1993), which is hereby incorporated by reference in its entirety). In addition to being more rapid, the peak intensity of phosphorylation was higher with bicarbonate treatment. The different kinetics and intensity of CREB activation by bicarbonate and $PGE_2$ revealed that, whereas sAC and tmACs may affect overlapping substrates, they may participate in distinct signal transduction cascades.

Example 9

CREB, sAC, and PKA Coexist in the Nucleus

Figure 3:
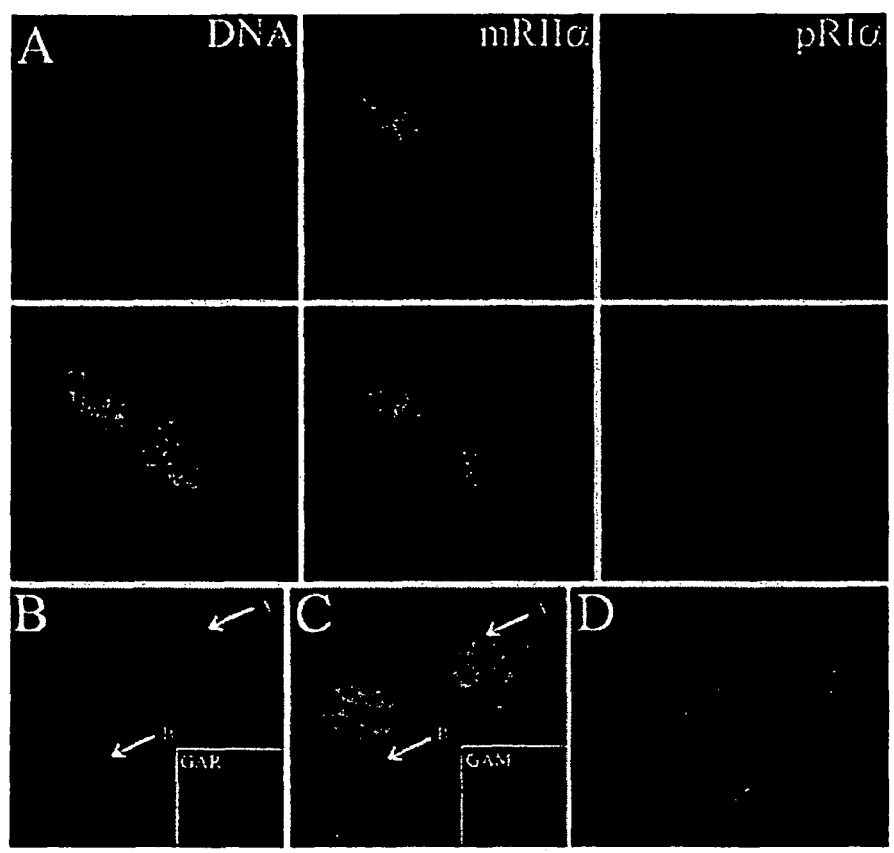
FIGS. 3A-D illustrate that immunocytochemistry detects both sAC and PKA in the mammalian cell nucleus.

Because CREB family members and sAC (Zippin et al., "Compartmentalization of Bicarbonate-Sensitive Adenylyl Cyclase in Distinct Signaling Microdomains," *FASEB J.* 17:82-84 (2003), which is hereby incorporated by reference in its entirety) reside inside the nucleus, it was reasoned that the accelerated kinetics and intensity of bicarbonate-induced CREB activation could occur if sAC and CREB coexisted in a signal transducing complex. A complete nuclear cAMP signaling cascade capable of phosphorylating CREB family proteins requires the presence of the cAMP-responsive PKA holoenzyme. Both catalytic and regulatory subunits of PKA have been immunologically (Kuettel et al., "Localization of Nuclear Subunits of Cyclic AMP-Dependent Protein Kinase by the Immunocolloidal Gold Method," *J. Cell Biol.* 101: 965-975 (1985); Jungmann et al., "Using Immunocolloidal Gold Electron Microscopy to Investigate cAMP-Dependent Protein Kinase Cellular Compartmentalization," *Methods Enzymol.* 159:225-235 (1988); Yang et al., "A-Kinase Anchoring Protein 100 (AKAP100) is localized in Multiple Subcellular Compartments in the Adult Rat Heart," *J. Cell Biol.* 142:511-522 (1998), which are hereby incorporated by reference in their entirety) and biochemically (Byus et al., "Direct Cytochemical Localization of Catalytic Subunits Dissociated from cAMP-Dependent Protein Kinase in Reuber H-35 Hepatoma Cells. II. Temporal and Spatial Kinetics," *J. Cell Biol.* 93:727-734 (1982); Murray et al., "Intracellular Kinetics of Free Catalytic Units Dissociated From Adenosine 3',5'-Monophosphate-Dependent Protein Kinase in Adrenocortical Tumor Cells (Y-1)," *Endocrinology* 116: 364-374 (1985); Zhang et al., "Nuclear Localization of Type II cAMP-Dependent Protein Kinase During Limb Cartilage Differentiation is Associated With a Novel Developmentally Regulated A-Kinase Anchoring Protein," *Dev. Biol.* 176:51-61 (1996); Constantinescu et al., "Ethanol-Induced Translocation of cAMP-Dependent Protein Kinase to the Nucleus. Mechanism and Functional Consequences," *J. Biol. Chem.* 274:26985-26991 (1999), which are hereby incorporated by reference in their entirety) detected inside the nucleus. Nuclear localization of the PKA holoenzyme has been described in lower eukaryotes (Griffioen et al., "Nutritional Control of Nucleocytoplasmic Localization of cAMP-Dependent Protein Kinase Catalytic and Regulatory Subunits in *Saccharomyces cerevisiae*," *J. Biol. Chem.* 275:1449-1456 (2000), which is hereby incorporated by reference in its entirety), but the nuclear presence of the PKA regulatory subunit, and the cAMP-responsive holoenzyme, has been questioned. The immunological examination of regulatory subunit localization was repeated and extended, and it was confirmed that PKA resided inside the nucleus of the human liver cell line Huh7 (FIG. 3A), in suspension HeLa cells (FIGS. 3B-C), and in a subset of cells within sectioned liver tissue (FIG. 4A). Confocal microscopy of Huh7 and HeLa cells, using polyclonal and monoclonal antibodies that recognize PKA regulatory subunit isoforms (RIα and RIIα), revealed distinctive cytoplasmic staining in accordance with accepted dogma (Alto et al., "Intracellular Targeting of Protein Kinases and Phosphatases," *Diabetes* 51(3):S385-S388 (2002), which is hereby incorporated by reference in its entirety; FIGS. 3A-C), but these regulatory subunit isoforms were also detected inside the nucleus (FIGS. 3A-C and FIG. 4A). In the case of suspension HeLa cells, it should be stressed that these optical slices were selected to illustrate the intranuclear staining of PKA. Slide preparation and imaging constraints caused PKA cytoplasmic staining to appear as a thin layer surrounding the nucleus (FIGS. 3B-C, arrows labeled A) and within the expanse of cytoplasm stretching out as these suspension cells adhere to the coverslip (FIGS. 3B-C, arrows labeled B).

Figure 4:
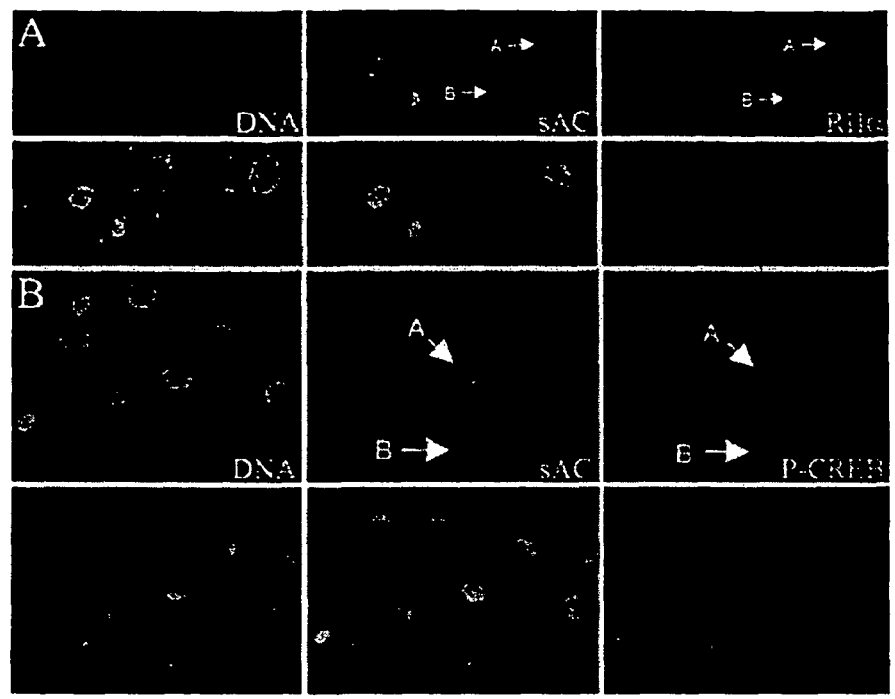
FIGS. 4A-B illustrate that activated CREB, sAC, and PKA are present within the same rat liver nuclei.

Nuclear staining of each isoform was distinct. RIIα was present in a diffuse pattern throughout the nucleus with small areas of enrichment (FIG. 3A, mRIIα; and FIG. 3B), whereas RIα was distributed in the nucleoplasm but more enriched in nucleoli (FIG. 3A, pRIα; and FIG. 3C). RIIα was also detected in the nuclei of a subset of rat liver primary hepatocytes (FIG. 4A). Consistent with Zippin et al., "Compartmentalization of Bicarbonate-Sensitive Adenylyl Cyclase in Distinct Signaling Microdomains," *FASEB J.* 17:82-84 (2003), which is hereby incorporated by reference in its entirety, sAC was also present in the nuclei of Huh7 cells (FIG. 3D) and a subset of rat liver hepatocytes (FIG. 4). PKA, sAC, and phosphorylated CREB seem to be coordinately localized; the subset of nuclei in rat liver hepatocytes and Huh7 cells positive for sAC protein (FIGS. 4A-B, arrows labeled A) also contained R subunit (FIG. 4A, arrows labeled A) and CREB phosphorylation (FIG. 4B, arrows labeled A), whereas nuclei not enriched for sAC displayed neither R subunit nor CREB phosphorylation (FIGS. 4A-B, arrows labeled B). Rat liver hepatocytes positive for sAC, PKA, and phospho-CREB represented ~10% of total hepatocytes, and any consistency with known liver anatomy has not yet been identified. These data demonstrated that nuclei contained all the components of a cAMP signaling cascade and suggested that sAC-generated cAMP is positioned to activate nuclear PKA holoenzymes to phosphorylate CREB proteins.

Example 10

Isolated Nuclei Contain Components of a cAMP Signaling Microdomain

Figure 5:
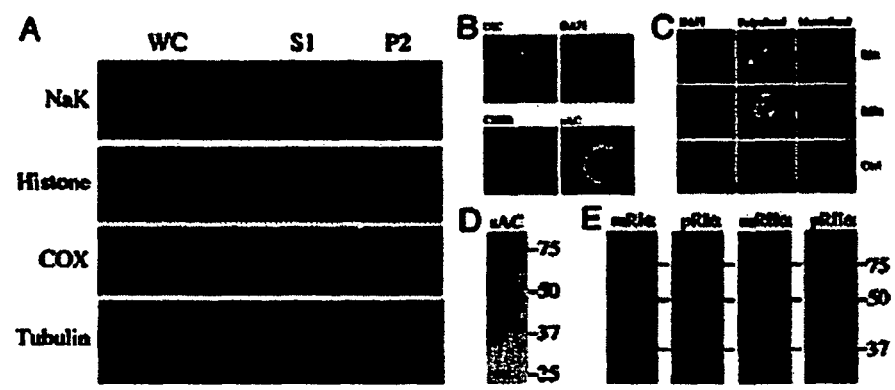
FIGS. 5A-E illustrate that sAC, PKA, and CREB coexist in mammalian cell nuclei.

Bicarbonate treatment of whole cells led to rapid induction of CREB phosphorylation (FIGS. 2A-B). To test whether the nuclear localized sAC and PKA were responsible for this bicarbonate-induced CREB activation, isolated nuclei was prepared from suspension HeLa cells, a cell line with well-established protocols for the isolation and enrichment of nuclei. Cells were lysed using digitonin, and nuclear preparations were purified by density centrifugation through an OptiPrep gradient. Western analyses of the same cell equivalents from each fraction, using cellular markers for different subcellular compartments (histone H1, NaK ATPase α1 subunit, cytochrome c oxidase subunit III [COX], and β-tubulin) confirmed that the nuclear fractions (P2) were positive for nuclear markers (histone) with undetectable levels of plasma membrane (NaK ATPase), mitochondrial (COX), or cytoplasmic (tubulin) contamination (FIG. 5A). To confirm that the P2 fraction did not contain any detectable mitochondria, a possible source of both sAC and PKA contamination, the P2 fraction was overloaded, but COX antigen was still not detected. Visual inspection and DAPI fluorescence confirmed that the final preparation was enriched for intact nuclei (FIGS. 5B-C), and, as expected, isolated nuclei contained both CREB and sAC proteins by immunocytochemistry (FIG. 5B) and Western blotting (FIG. 5D).

Consistent with the aforementioned staining patterns (FIGS. 3A-C), RIIα immunostaining was present throughout the nucleus, whereas RIα appeared enriched within the nucleolus (FIG. 5C). PKA RIα and RIIα were also detected by Western analysis as a single band of the predicted molecular mass in the P2 lysate, using monoclonal and polyclonal antibodies (FIG. 5E), confirming the specificities of these antibodies for immunostaining. Because the staining patterns of isolated HeLa cell nuclei (FIG. 5C) reflected the immunostaining pattern observed in intact HeLa cells (FIG. 5B-C), it was concluded that the isolation and enrichment of nuclei had little effect on nucleoplasm architecture.

Example 11 sAC Represents the Only Source of cAMP Detectable in Isolated Nuclei

Zippin et al., "Compartmentalization of Bicarbonate-Sensitive Adenylyl Cyclase in Distinct Signaling Microdomains," *FASEB J.* 17:82-84 (2003), which is hereby incorporated by reference in its entirety, previously demonstrated that sAC activity was present in COS7 cell nuclei. The results described in Example 10 showed that bicarbonate-responsive sAC was the only source of cAMP in nuclei isolated from suspension HeLa cells. Whereas forskolin potently stimulated cAMP production in whole cell lysates, there was no significant increase in cAMP elicited by forskolin in isolated nuclei. There was a significant level of basal adenylyl cyclase activity in isolated nuclei, which was stimulated by bicarbonate addition. Both the bicarbonate-stimulated and basal activities were inhibited by sAC-selective inhibitors. Several sAC inhibitors (Table 1), inert toward tmACs, were identified in a screen of a combinatorial chemical library. In the presence of representative inhibitors, the cAMP generated in the presence of bicarbonate in P2 nuclei was reduced to a level below that of basal. These results indicated that, in addition to mediating the bicarbonate-induced increase in cAMP in isolated nuclei, sAC is also responsible for the observed basal adenylyl cyclase activity.

TABLE 1

Compounds That Modulate sAC Activity in vitro and in vivo

| Name | Structure | in vitro $IC_{50}{}^a$ | | | | in vivo $IC_{50}{}^b$ | |
|---|---|---|---|---|---|---|---|
| | | pure sAC | pure sol.AC7 | sAC in extracts | tmAC in extracts | sAC (basal) | tmAC (FSK) |
| KH1 | (structure) | 23 μM | >200 μM | | | >500 μM | >500 μM |
| KH2 | (structure) | 2 μM | >400 μM | >>100 | >>100 | >500 μM | >500 μM |
| KH3 | (structure) | 8 μM | >500 μM | >>100 | >>100 | >500 μM | >500 μM |

TABLE 1-continued

Compounds That Modulate sAC Activity in vitro and in vivo

| Name | Structure | in vitro IC$_{50}$$^a$ | | | | in vivo IC$_{50}$$^b$ | |
|---|---|---|---|---|---|---|---|
| | | pure sAC | pure sol.AC7 | sAC in extracts | tmAC in extracts | sAC (basal) | tmAC (FSK) |
| KH4 | | 6 μM | >>27 μM | >>100 | >>100 | >500 μM | >500 μM |
| KH7 | | 1 μM | >>55 μM | <10 μM | >>100 μM | 10 μM–30 μM | >500 μM |
| KH7.05 | | ~30 | | | | 30 μM | >200 μM |
| KH7.06 | | ~30 | | | | | |

TABLE 1-continued

Compounds That Modulate sAC Activity in vitro and in vivo

| Name | Structure | in vitro IC$_{50}$[a] | | | | in vivo IC$_{50}$[b] | |
|---|---|---|---|---|---|---|---|
| | | pure sAC | pure sol.AC7 | sAC in extracts | tmAC in extracts | sAC (basal) | tmAC (FSK) |
| KH7.07 | 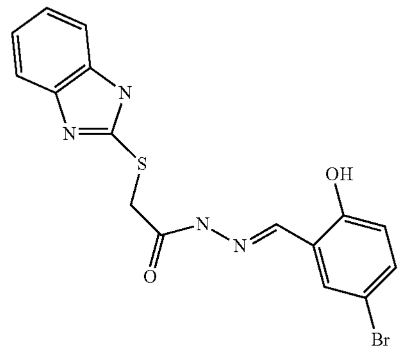 [SMILES: O=C(CSc1nc2ccccc2[nH]1)N/N=C/c1cc(Br)ccc1O] | 30 μM | | | | 30 μM | >200 μM |
| KH7.10 | 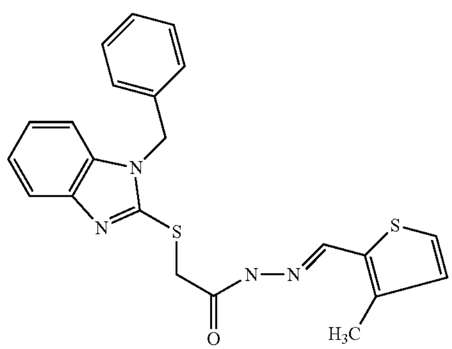 [SMILES: Cc1ccsc1/C=N/NC(=O)CSc1nc2ccccc2n1Cc1ccccc1] | 80 | | | | | |
| KH7.11 | 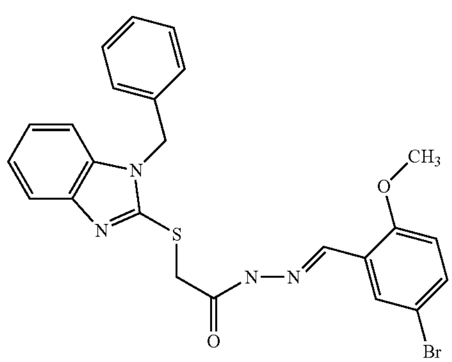 [SMILES: COc1ccc(Br)cc1/C=N/NC(=O)CSc1nc2ccccc2n1Cc1ccccc1] | 65 | | | | | |
| KH7.12 | 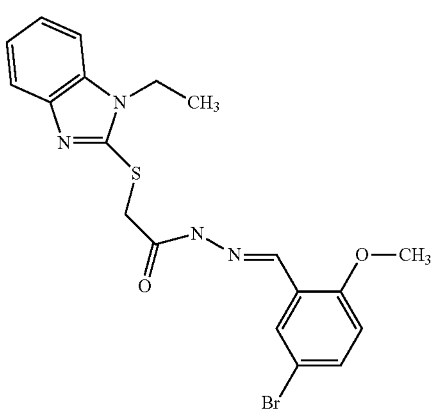 [SMILES: CCn1c(SCC(=O)N/N=C/c2cc(Br)ccc2OC)nc2ccccc21] | 30 | | | | | |

TABLE 1-continued

Compounds That Modulate sAC Activity in vitro and in vivo

| | | in vitro $IC_{50}{}^a$ | | | | in vivo $IC_{50}{}^b$ | |
|---|---|---|---|---|---|---|---|
| Name | Structure | pure sAC | pure sol.AC7 | sAC in extracts | tmAC in extracts | sAC (basal) | tmAC (FSK) |
| KH7.13 | | | | 75 | | | |

[a] In vitro $IC_{50}$ refers to the concentration that inhibits 50% of the in vitro cyclase activity of purified sperm isoform of sAC protein (pure sAC), purified solubilized version of Type VII tmAC (sol.AC7), whole cell extracts from cells overexpressing sperm sAC cDNA (sAC in extracts), or cells overexpressing Type II tmAC (tmAC in extracts).
[b] In vivo $IC_{50}$ refers to the concentration required to inhibit 50% of the cAMP forming activity inside cells stably overexpressing sAC [sAC(basal)] or cells stimulated with forskolin [tmAC (FSK)]. (Forskolin exclusively stimulates tmACs.)

Example 12

Bicarbonate Induces CREB Phosphorylation in Isolated Nuclei

Figure 6:
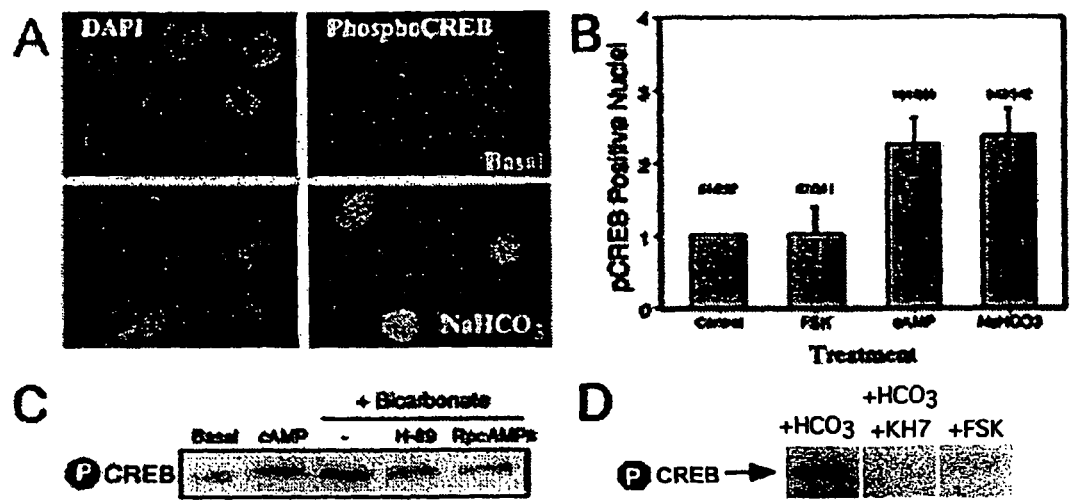
FIGS. 6A-D illustrate that isolated nuclei contain a bicarbonate-responsive cAMP signaling microdomain dependent on both sAC and PKA. Equal aliquots of nuclei-enriched P2 were incubated with 40 mM NaCl (Basal), 10 µM forskolin (FSK), 1 mM 8-Br cAMP (cAMP), or 40 mM of sodium bicarbonate (NaHCO$_3$) for 10 min, smeared on a chilled glass slide, placed at −20° C., and immunostained for CREB family member phosphorylation using phospho-CREB-specific polyclonal antisera (FIGS. 6A-B). Intact nuclei were confirmed by DAPI staining (FIG. 6A; left).

CREB phosphorylation in isolated nuclei was assayed by immunocytochemistry using phospho-CREB-specific antisera (FIGS. 6A-B). Nuclei incubated in the presence of either bicarbonate or cAMP displayed at least a twofold rise in the percentage of phospho-CREB-positive nuclei relative to untreated nuclei (basal; FIG. 6B). As expected, due to the lack of tmACs in isolated nuclei, the number of nuclei positive for CREB phosphorylation was unaffected by forskolin. These data demonstrated that a bicarbonate-responsive signaling cascade leading to CREB phosphorylation was wholly contained within the mammalian cell nucleus. In contrast, the hormone and forskolin-responsive tmAC-defined cascade is only functional in a whole cell context.

Example 13

Nuclear sAC Activates CREB Via Nuclear PKA

To facilitate the use of pharmacological reagents to further evaluate bicarbonate-induced CREB phosphorylation, CREB phosphorylation by Western analysis was monitored (FIGS. 6C-D). Similar to the observations using immunocytochemistry (described in Example 12), treatment of isolated nuclei with bicarbonate or 8-Br-cAMP elicited a 27- or 30-fold increase in CREB phosphorylation, respectively (FIG. 6C). Once again, forskolin, which had a potent effect in a whole cell context (FIG. 1), elicited no significant stimulation of CREB phosphorylation in isolated nuclei (FIG. 6D).

Next, it was confirmed that the effects of bicarbonate on CREB phosphorylation were mediated by nuclear sAC and PKA. CREB phosphorylation induced by bicarbonate was substantially reduced by the PKA inhibitors, H89 (50%) and RpcAMPs (70%; FIG. 6C), revealing the involvement of cAMP-responsive PKA holoenzyme. A representative chemical inhibitor, KH7, was effective in preventing bicarbonate-induced CREB phosphorylation (FIG. 6D), demonstrating, once again, that sAC is responsible for the bicarbonate-stimulated cAMP-dependent phosphorylation of CREB in the mammalian cell nucleus.

Example 14

Bicarbonate-Responsive sAC Defines a Nuclear cAMP Microdomain

Most cellular pathways in eukaryotic cells are impacted by cAMP. Effectors of cAMP mediate processes at both the plasma membrane and multiple, distinct intracellular sites. It has been widely assumed that cAMP is generated exclusively at the plasma membrane by G protein-regulated tmACs, and the second messenger then diffuses from the cell membrane through the cytosol to its intracellular targets. However, FRET-based (Bacskai et al., "Spatially Resolved Dynamics of Camp and Protein Kinase A Subunits in Aplysia Sensory Neurons," *Science* 260:222-226 (1993); Zaccolo et al., "Discrete Microdomains With High Concentration of cAMP in Stimulated Rat Neonatal Cardiac Myocytes," *Science* 295:1711-1715 (2002), which are hereby incorporated by reference in their entirety) and biochemical (Rich et al., "Cyclic Nucleotide-Gated Channels Colocalize With Adenylyl Cyclase in Regions of Restricted cAMP Diffusion," *J. Gen. Physiol.* 116:147-161 (2000); Rich et al., "A Uniform Extracellular Stimulus Triggers Distinct cAMP Signals in Different Compartments of a Simple Cell." *Proc. Natl. Acad. Sci. USA* 98:13049-13054 (2001), which are hereby incorporated by reference in their entirety) methods for observing intracellular cAMP concentrations reveal that the second messenger generated by tmACs does not diffuse far from its site of synthesis. It has been recently demonstrated that sAC is localized at multiple, subcellular compartments throughout the cell including mitochondria, centrioles, mitotic spindles, mid-bodies, and nuclei (Zippin et al., "Compartmentalization of Bicarbonate-Sensitive Adenylyl Cyclase in Distinct Signaling Microdomains," *FASEB J.* 17:82-84 (2003), which is hereby incorporated by reference in its entirety), each of which contains targets of cAMP. These data suggest that the cell may contain multiple, independently modulated cAMP signaling microdomains; targets near the plasma membrane would depend on tmACs for second messenger generation, whereas targets inside the cell would be modulated by sAC-generated cAMP (Wuttke et al., "Bicarbonate-Regulated Soluble Adenylyl Cyclase," *JOP* 2:154-158 (2001); Zippin et al., "Compartmentalization of Bicarbonate-Sensitive Adenylyl Cyclase in Distinct Signaling Microdomains," *FASEB J.* 17:82-84 (2003), which are hereby incorporated by reference in their entirety). The data disclosed herein support this hypothesis by demonstrating the existence of a sAC-defined nuclear cAMP signaling microdomain, which can lead to CREB activation.

The nuclear cAMP signaling cascade induced by bicarbonate produced a rapid activation of CREB family members in both whole cells and nuclei, whereas $PGE_2$ and forskolin, tmAC-specific activators, produced a delayed response exclusively in whole cells. Therefore, cAMP-mediated activation of CREB family members by tmACs and sAC proceed via independent pathways. CREB activation by hormones or neurotransmitters via tmACs apparently requires time for movement of PKA catalytic subunit from the plasma membrane into the nucleus (Riabowol et al., "The Catalytic Subunit of cAMP-Dependent Protein Kinase Induces Expression of Genes Containing cAMP-Responsive Enhancer Elements," *Nature* 336:83-86 (1988); Hagiwara et al., "Coupling of Hormonal Stimulation and Transcription Via the Cyclic AMP-Responsive Factor CREB is Rate Limited by Nuclear Entry of Protein Kinase A," *Mol. Cell. Biol.* 13:4852-4859 (1993), which are hereby incorporated by reference in their entirety). This delayed activation is consistent with hormonal control of gene expression providing a long-term response to predominantly sustained extracellular signals (Bailey et al., "Toward a Molecular Definition of Long-Term Memory Storage," *Proc. Natl. Acad. Sci. USA* 93:13445-13452 (1996), which is hereby incorporated by reference in its entirety). In contrast, the newly described nuclear sAC activation pathway proceeds rapidly without requiring the translocation of any constituent. In this regard, the sAC nuclear microdomain is capable of responding quickly to subtle fluctuations in intrinsic signals, such as local intracellular concentrations of bicarbonate and calcium.

In tissues, sAC is not present within the nucleus of every cell. In liver, sAC appeared to be predominantly extra-nuclear but enriched in a subset of the nuclei (FIGS. 4A-B, arrows labeled A). PKA holoenzyme appeared to be enriched within the same subset of nuclei (FIG. 4A, arrows labeled A), and interestingly, these are the nuclei that were also positive for CREB phosphorylation (FIG. 4B, arrows labeled A). The presence of both positive and negative nuclei for sAC, PKA, and CREB phosphorylation in the same tissue suggests that there may be coordinated regulation of the presence of this newly described nuclear signaling microdomain.

The demonstration that bicarbonate treatment of whole cells led to activation of the CREB family of transcription factors revealed that bicarbonate itself induces a signal transduction cascade. Cellular bicarbonate levels reflect intracellular pH as well as $CO_2$ generation (Bevensee et al., "Control of Intracellular pH," in Seldin, eds., *The Kidney*, Vol. I., Lippincott Williams & Wilkins, Philadelphia, Pa. pp. 391-442 (2000), which is hereby incorporated by reference in its entirety); therefore, bicarbonate signaling pathways would respond to a wide variety of cellular transitions. Immunostaining revealed that sAC is present at mitochondria, centrioles, mitotic spindles, and mid-bodies (Zippin et al., "Compartmentalization of Bicarbonate-Sensitive Adenylyl Cyclase in Distinct Signaling Microdomains," *FASEB J.* 17:82-84 (2003), which is hereby incorporated by reference in its entirety), suggesting the existence of multiple cAMP signaling microdomains within a single cell. A remaining challenge will be to determine whether sAC molecules in these different microdomains are subject to independent and unique modes of regulation, permitting a variety of distinct responses independently mediated by the same second messenger.

Example 15

Soluble Adenylyl Cyclase as the Source of Glucose-Induced cAMP Required for Glucose-Stimulated Insulin Secretion Beta-cells of the islets of Langerhans secrete insulin in response to nutrient secretagogues, such as glucose. Despite knowing for over thirty years that glucose-stimulated insulin secretion (GSIS) is accompanied by a rise in the second messenger cAMP (Charles et al., "Adenosine 3',5'-Monophosphate in Pancreatic Islets: Glucose-Induced Insulin Release," *Science* 179:569-571 (1973); Charles et al., "Insulin Secretion. Interrelationships of Glucose, Cyclic Adenosine 3:5-Monophosphate, and Calcium," *J. Biol. Chem.* 250: 6134-6140 (1975); Rutter, "Nutrient-Secretion Coupling in the Pancreatic Islet Beta-Cell: Recent Advances," *Mol Aspects Med.* 22:247-284 (2001), which are hereby incorporated by reference in their entirety), the source of cAMP and its connection to glucose metabolism has remained undefined (Rutter, "Nutrient-Secretion Coupling in the Pancreatic Islet Beta-Cell: Recent Advances," *Mol Aspects Med.* 22:247-284 (2001), which is hereby incorporated by reference in its entirety). The second messenger is essential for GSIS; membrane permeable cAMP analogs elicit insulin secretion (Schubart et al., "Cyclic Adenosine 3':5'-Monophosphate-Mediated Insulin Secretion and Ribosomal Protein Phosphorylation in a Hamster Islet Cell Tumor," *J. Biol. Chem.* 252:92-101 (1977), which is hereby incorporated by reference in its entirety), and two of the three known targets of cAMP, PKA and EPAC, are required for normal insulin release. Until recently, G protein regulated tmACs constituted the only known sources of cAMP in beta-cells, but cAMP generated by tmACs is unable on its own to elicit insulin secretion (Rutter, "Nutrient-Secretion Coupling in the Pancreatic Islet Beta-Cell: Recent Advances," *Mol. Aspects Med.* 22:247-284 (2001), which is hereby incorporated by reference in its entirety). tmAC modulation by hormones, such as glucagon and incretins, potentiates glucose-induced insulin secretion, yet constitutive activation of tmACs in beta-cells did not stimulate insulin release in low glucose (Delmeire et al., "Type VIII Adenylyl Cyclase in Rat Beta Cells: Coincidence Signal Detector/Generator for Glucose and GLP-1*," Diabetologia* 46:1383-1393 (2003); Ma et al., "Constitutively Active Stimulatory G-Protein Alpha S in Beta-Cells of Transgenic Mice Causes Counterregulation of the Increased Adenosine 3',5'-Monophosphate and Insulin Secretion," *Endocrinology* 134:42-47 (1994); Rutter, "Nutrient-Secretion Coupling in the Pancreatic Islet Beta-Cell: Recent Advances," *Mol. Aspects Med.* 22:247-284 (2001), which are hereby incorporated by reference in their entirety) nor did it affect glucose tolerance in mice (a et al., "Constitutively Active Stimulatory G-Protein Alpha S in Beta-Cells of Transgenic Mice Causes Counterregulation of the Increased Adenosine 3',5'-Monophosphate and Insulin Secretion," *Endocrinology* 134:42-47 (1994), which is hereby incorporated by reference in its entirety).

An additional source of cAMP in mammalian cells, "soluble" adenylyl cyclase (sAC), has been identified (Buck et al., "Cytosolic Adenylyl Cyclase Defines a Unique Signaling Molecule in Mammals," *Proc. Natl. Acad. Sci. USA* 96:79-84 (1999), which is hereby incorporated by reference in its entirety). sAC activity is regulated by the intracellular signaling molecules bicarbonate (Chen et al., "Soluble Adenylyl Cyclase as an Evolutionarily Conserved Bicarbonate Sensor," *Science* 289:625-628 (2000), which is hereby incorporated by reference in its entirety) and calcium (Jaiswal et al., "Calcium Regulation of the Soluble Adenylyl Cyclase Expressed in Mammalian Spermatozoa," *Proc. Natl. Acad. Sci. USA* 100:10676-10681 (2003); Litvin et al., "Kinetic Properties of "Soluble" Adenylyl Cyclase. Synergism Between Calcium and Bicarbonate," *J. Biol. Chem.* 278:15922-15926 (2003), which are hereby incorporated by reference in their entirety), both of which are essential for normal glucose-induced insulin release (Parkkila et al., "Expression of Carbonic Anhydrase V in Pancreatic Beta Cells Suggests Role for Mitochondrial Carbonic Anhydrase in Insulin Secretion," *J. Biol. Chem.* 273:24620-24623 (1998); Rutter, "Nutrient-Secretion Coupling in the Pancreatic Islet Beta-Cell: Recent Advances," *Mol. Aspects Med.* 22:247-284 (2001), which are hereby incorporated by reference in their entirety). In contrast to plasma membrane bound tmACs, sAC is localized to intracellular compartments containing cAMP targets (Zippin et al., "Compartmentalization of Bicarbonate-Sensitive Adenylyl Cyclase in Distinct Signaling Microdomains," *FASEB J.* 17:82-84 (2003), which is hereby incorporated by reference in its entirety) where it appears to be the source of locally acting second messenger (Bundey et al., "Discrete Intracellular Signaling Domains of Soluble Adenylyl Cyclase: Camps of cAMP?" *Sci STKE* 2004 (231):pe19 (2004); Zippin et al., "Bicarbonate-Responsive "Soluble" Adenylyl Cyclase Defines a Nuclear cAMP Microdomain," *J. Cell Biol.* 164:527-534 (2004), which are hereby incorporated by reference in their entirety). The data in this example shows that sAC is present in beta-cells and is localized near insulin secretory granules. Proximity to insulin secretory granules and regulation by intracellular signals downstream from glucose metabolism suggested sAC could be a local source of cAMP mediating glucose-elicited insulin secretion. Using small molecule inhibitors which distinguish between sAC and tmACs, sAC was identified as the source of glucose-induced cAMP in beta-cells that is essential for glucose-induced insulin secretion in insulinoma cell lines and isolated islets and for normal glucose homeostasis and insulin secretion in mice.

Cell Culture

INS-1E cells (passage 140-150) were cultured as previously described in Merglen et al., "Glucose Sensitivity and Metabolism-Secretion Coupling Studied During Two-Year Continuous Culture in INS-1E Insulinoma Cells," *Endocrinology* 145:667-678 (2004), which is hereby incorporated by reference in its entirety. Briefly, cells were passaged every three days and cultured under 5% $CO_2$ with RPMI containing 10 mM Hepes, 50 µM β-mercaptoethanol, and 10% FBS. sAC overexpressing stable cell lines were constructed by infecting INS-1E cells with a lentiviral-based vector (Gateway Cloning System, Invitrogen) containing the fill length sAC cDNA. Single clones (SF2 and SF5) were selected with blasticidin (1 µg/ml).

Immunocytochemistry

Sectioned rat pancreas (6 µm), BetaTC6, RINm5F, or INS-1E cells were fixed for 15 minutes in 4% paraformaldehyde, washed, permeabilized in 0.1% Triton X-100, washed, blocked in 2% BSA, and then probed with biotinylated R52 (Zippin et al., "Compartmentalization of Bicarbonate-Sensitive Adenylyl Cyclase in Distinct Signaling Microdomains," *FASEB J.* 17:82-84 (2003), which is hereby incorporated by reference in its entirety), anti-C-term polyclonal (Zippin et al., "Compartmentalization of Bicarbonate-Sensitive Adenylyl Cyclase in Distinct Signaling Microdomains," *FASEB J.* 17:82-84 (2003), which is hereby incorporated by reference in its entirety), or anti-insulin (polyclonal Santa Cruz, H-89 or monoclonal Sigma) overnight. Sections and coverslips were then washed and probed with appropriate secondary antibodies (1:200, Alexafluor, Molecular Probes). Images were recorded on a Nikon microscope.

Adenylyl Cyclase Assays and cAMP Determinations

In vitro adenylyl cyclase assays were performed on purified recombinant human $sAC_t$ protein as previously described in Litvin et al., "Kinetic Properties of "Soluble" Adenylyl Cyclase. Synergism Between Calcium and Bicarbonate," *J. Biol. Chem.* 278:15922-15926 (2003), which is hereby incorporated by reference in its entirety, or on whole cell lysates of INS-1E cells lysed in 50 mM Tris-HCl pH7.5, 0.5 mM EDTA with protease inhibitors. Adenylyl cyclase activity was measured as previously described (Buck et al., "Cytosolic Adenylyl Cyclase Defines a Unique Signaling Molecule in Mammals," *Proc. Natl. Acad. Sci. USA* 96:79-84 (1999); Chen et al., "Soluble Adenylyl Cyclase as an Evolutionarily Conserved Bicarbonate Sensor," *Science* 289:625-628 (2000), which are hereby incorporated by reference in their entirety). In vivo cAMP accumulation was measured in cells pre-incubated in IBMX (0.5 mM) for 10 minutes, followed by the addition of stimuli for 15 minutes. Intracellular cAMP was determined in cells lysed with 0.1 M HCl using Correlate-EIA Direct cAMP Assay (Assay Designs, Inc.).

Pancreatic Islets Isolation

Islets from C57B1/6 adult male mice were isolated by digestion of pancreas with Collagenase P and DNase I (Roche Diagnostics, Basel, Switzerland), as described previously in Lacy et al., "Method for the Isolation of Intact Islets of Langerhans From the Rat Pancreas," *Diabetes* 16:35-39 (1967), which is hereby incorporated by reference in its entirety. After several washes with Hank's Balanced Salt Solution, islets were hand-picked and 15-20 islets were distributed into each well of a 12 well plate to adhere overnight in RPMI-1640 media supplemented with 10 mM HEPES, 5.6 mM glucose, 10% FBS, 2 mM L-glutamine, 1 mM sodium pyruvate, and antibiotics.

Insulin Release

Insulin release in INS-1E cells was performed as previously described in Antinozzi et al. "Mitochondrial Metabolism Sets the Maximal Limit of Fuel-Stimulated Insulin Secretion in a Model Pancreatic Beta Cell: A Survey of Four Fuel Secretagogues," *J. Biol. Chem.* 277:11746-11755 (2002), which is hereby incorporated by reference in its entirety. Briefly, cells (passage 140-150) were plated at $2.5 \times 10^5$ cells/well in a 24 well plate and permitted to recover for two days. Cells were glucose starved by incubation for 1 hour in the presence of 2.5 mM glucose KRB medium supplemented with 2 mM sodium bicarbonate, 10 mM Hepes, and 0.1% BSA. After washing, cells were incubated in KRB with either 2.5 mM or 16 mM glucose in the presence of either vehicle control (DMSO or MeOH) or indicated drug. After the indicated time, removed media was cleared of cell debris and secreted insulin was measured by Insulin ELISA kit (Linco Research, St. Charles, Mo., or ALPCO, Windham, N.H.). If cAMP was to be concomitantly measured, cells were pre-treated with IBMX for the final 10 minutes of the glucose starvation and IBMX was included in all subsequent incubations. For the washout experiment, subsequent to initial insulin determination, cells treated with KH7 were placed in fresh KRB (2.5 mM glucose) for an additional hour and insulin release was measured as above in the absence of any added drug. For transferrin recycling, loading of cells with $I^{125}$ transferrin was performed during hour incubation in 2.5 mM glucose KRB. Media was then changed to 2.5 mM glucose KRB with DMSO or KH7 and transferrin recycling measured as previously described in Johnson et al., "A Di-Leucine Sequence and a Cluster of Acidic Amino Acids are Required for Dynamic Retention in the Endosomal Recycling Compartment of Fibroblasts," *Mol. Biol. Cell* 12:367-381 (2001), which is hereby incorporated by reference in its entirety.

Insulin release from isolated islets was performed in 12 well plates. Islets were preincubated in KRB (2.8 mM glucose) for 1 hour followed by incubation for 30 minutes in 2.8 mM glucose KRB in the presence of drug. The same wells were then incubated for an additional 30 minutes in 16.7 mM glucose KRB in the presence of the same drugs. Media was removed, cleared of cells, and insulin was measured.

Glucose Tolerance

C57Bl/6 adult male mice were maintained on a 12 hour light/dark cycle, with free access to water and standard laboratory chow (Research Animal Resource Center, Weill Medical College of Cornell University). Animals were treated in accordance with our institutions guidelines. After a 14-16 hour overnight fast with free access to water, blood was removed from the tail vein for glucose (Hemocue B-Glucose Microcuvette and Analyzer; Hemocue, Inc., Lake Forest, Calif.) and insulin (Rat/Mouse Insulin ELISA Kit; Linco Research) measurements. Mice then received an i.p injection of 100 mM KH7 (100 µmoles/kg) or vehicle control. Twenty minutes later, both groups were injected i.p. with 1 g/kg glucose (20% solution). Blood samples were taken from the tail vein at times indicated, and glucose and insulin were quantitated according to manufacturer's instructions.

sAC as the Source of Glucose-Induced cAMP Required for GSIS

Figure 7:
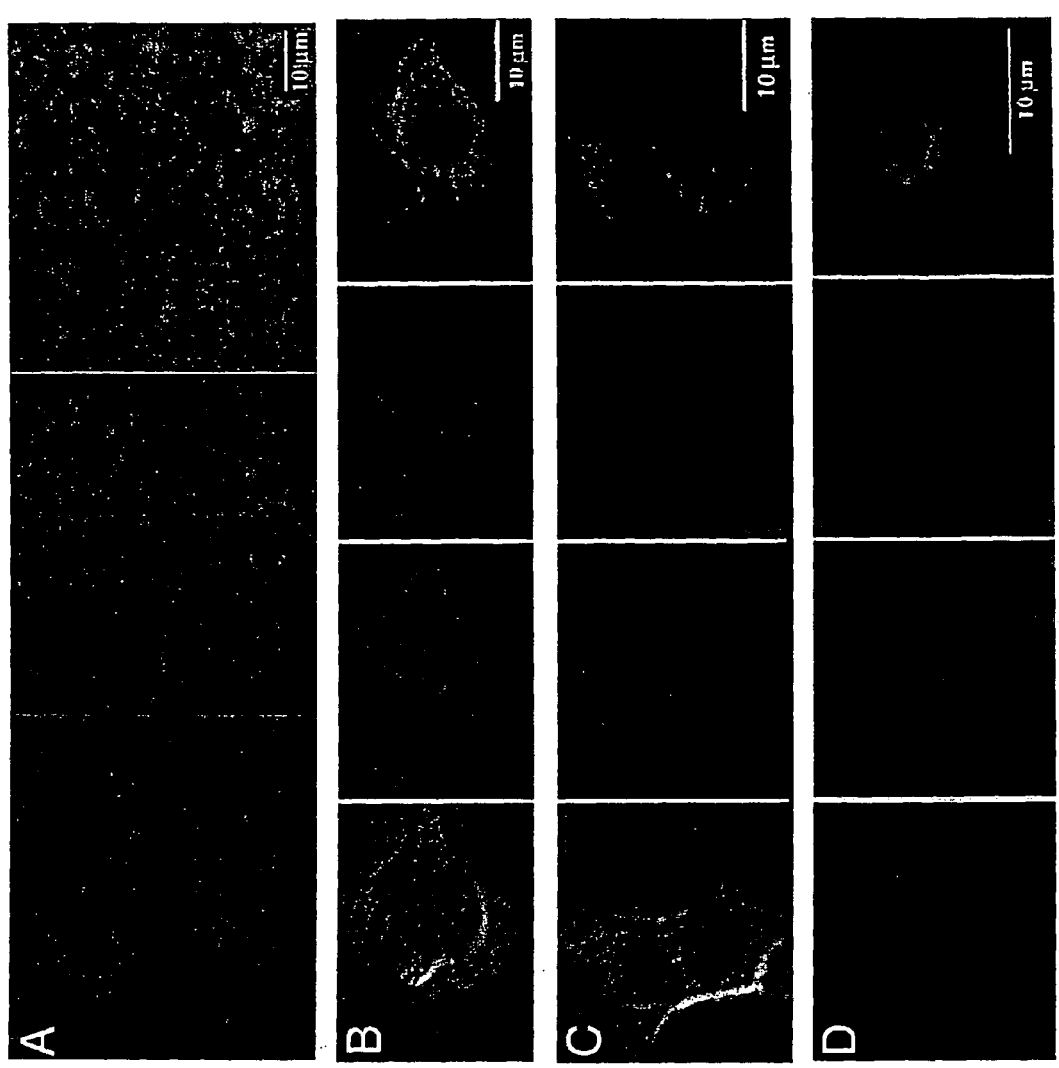
FIGS. 7A-D demonstrate that sAC is present in the Islets of Langerhans and is localized to insulin secretory granules in beta-cells.

The mRNA for sAC was detected in insulinoma cell lines including INS-1E cells. To examine protein localization, pancreatic islets and insulinoma cell lines were immunostained with multiple monoclonal and polyclonal antibodies directed against different sAC epitopes. sAC protein was detected throughout the cytoplasm of endocrine and exocrine pancreas and in the nuclei of a subset of islet cells (FIG. 7A). Expression in a subset of nuclei is consistent with the observations in liver (see Example 9). Co-staining with insulin (FIG. 7A), glucagon, and somatostatin revealed that sAC was not exclusively localized to any specific cell type but was evenly distributed in all cells of the islet. To examine the localization of sAC within insulin secreting beta-cells at higher resolution, sAC in beta-cell lines were immunostained. In BetaTC6 (FIG. 7B), RINm5F (FIG. 7C), and INS-1E cells (FIG. 7D), sAC exhibited a punctate staining pattern throughout the cytoplasm which co-localized with insulin secretory granules (FIGS. 7B-D). Recent models of cAMP signal transduction depend upon discrete signaling microdomains where the second messenger diffuses only short distances to its targets (Bundey et al., "Discrete Intracellular Signaling Domains of Soluble Adenylyl Cyclase: Camps of cAMP?" *Sci STKE* 2004, pe19 (2004); Rich et al., "Cyclic Nucleotide-Gated Channels Colocalize With Adenylyl Cyclase in Regions of Restricted cAMP Diffusion, " *J. Gen. Physiol.* 116:147-161 (2000); Rich et al., "A Uniform Extracellular Stimulus Triggers Distinct cAMP Signals in Different Compartments of a Simple Cell," *Proc. Natl. Acad. Sci. USA* 98:13049-13054 (2001); Zaccolo et al., "Discrete Microdomains With High Concentration of cAMP in Stimulated Rat Neonatal Cardiac Myocytes," *Science* 295:1711-1715 (2002); Zippin et al., "Bicarbonate-Responsive "Soluble" Adenylyl Cyclase Defines a Nuclear cAMP Microdomain," *J. Cell Biol.* 164:527-534 (2004), which are hereby incorporated by reference in their entirety). The observed proximity of sAC to insulin secretory granules, which contain cAMP effector proteins important in insulin release (Ammala et al., "Calcium-Independent Potentiation of Insulin Release by Cyclic AMP in Single Beta-Cells," *Nature* 363:356-358 (1993); Fujimoto et al., "Piccolo, A $Ca^{2+}$ Sensor in Pancreatic Beta-Cells. Involvement of cAMP-GEFII.Rim2. Piccolo Complex in cAMP-Dependent Exocytosis," *J. Biol. Chem.* 277:50497-50502 (2002); Holz, "EPAC: A New cAMP-Binding Protein in Support of Glucagon-Like Peptide-1 Receptor-Mediated Signal Transduction in the Pancreatic Beta-Cell," *Diabetes* 53:5-13 (2004); Kang et al., "EPAC-Selective cAMP Analog 8-pCPT-2'-O-Me-cAMP as a Stimulus for $Ca^{2+}$-Induced $Ca^{2+}$ Release and Exocytosis in Pancreatic Beta-Cells," *J. Biol. Chem.* 278: 8279-8285 (2003); Ozaki et al., "cAMP-GEFII is a Direct Target of cAMP in Regulated Exocytosis," *Nat. Cell. Biol.* 2:805-811 (2000); Renstrom et al., "Protein Kinase A-Dependent and -Independent Stimulation of Exocytosis by cAMP in Mouse Pancreatic B-Cells," *J. Physiol.* 502 (Pt 1):105-118 (1997); Shibasaki et al., "Interaction of ATP Sensor, cAMP Sensor, $Ca^{2+}$ Sensor, and Voltage-Dependent $Ca^{2+}$ Channel in Insulin Granule Exocytosis," *J. Biol. Chem.* 279:7956-7961 (2004), which are hereby incorporated by reference in their entirety), suggested that sAC generated cAMP could participate in insulin secretion.

Figure 8:
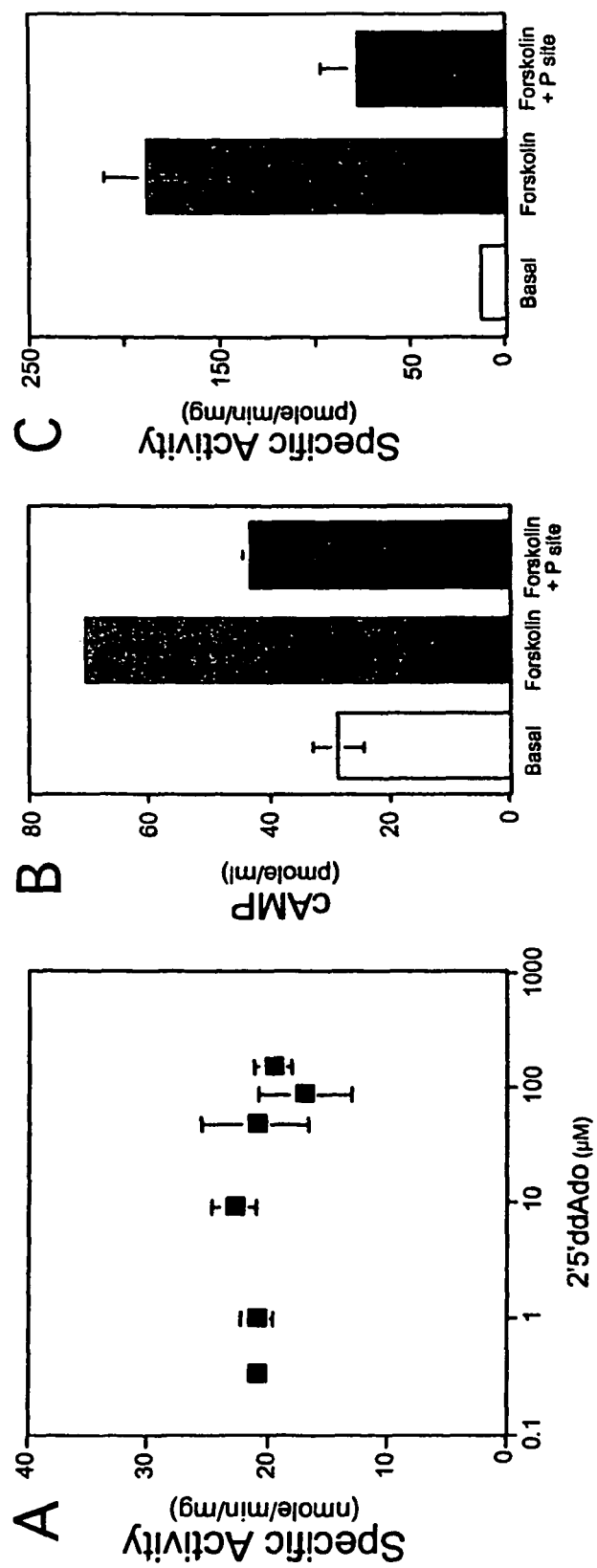
FIGS. 8A-C illustrate that the P site inhibitor, 2'5'ddAdo, is a potent inhibitor of tmACs but is inert towards sAC.

To distinguish between sources of cAMP in mammalian cells, a cadre of small molecules capable of differentiating between the two classes of adenylyl cyclases, G protein responsive tmACs and bicarbonate (Chen et al., "Soluble Adenylyl Cyclase as an Evolutionarily Conserved Bicarbonate Sensor," *Science* 289:625-628. (2000), which is hereby incorporated by reference in its entirety) and calcium responsive sAC (Jaiswal et al., "Calcium Regulation of the Soluble Adenylyl Cyclase Expressed in Mammalian Spermatozoa," *Proc. Natl. Acad. Sci. USA* 100:10676-10681 (2003); Litvin et al., "Kinetic Properties of "Soluble" Adenylyl Cyclase. Synergism Between Calcium and Bicarbonate," *J. Biol. Chem.* 278:15922-15926 (2003), which are hereby incorporated by reference in their entirety) were applied. P site inhibitors are a family of small molecules, predominantly adenosine analogs, which potently inhibit tmACs ($IC_{50}$=3-16 µM) (Johnson et al., "Isozyme-Dependent Sensitivity of Adenylyl Cyclases to P-site-Mediated Inhibition by Adenine Nucleosides and Nucleoside 3'-Polyphosphates," *J. Biol Chem.* 272:8962-8966 (1997), which is hereby incorporated by reference in its entirety). P site inhibitors are significantly less potent towards sAC (Gille et al., "Differential Inhibition of Adenylyl Cyclase Isoforms and Soluble Guanylyl Cyclase by Purine and Pyrimidine Nucleotides," *J. Biol Chem.* 279:19955-19969 (2004), which is hereby incorporated by reference in its entirety), and it was determined that 2'5' dideoxyadenosine (2'5'ddAdo) did not significantly affect sAC at concentrations up to 300 µM (FIGS. 8A-C). A dearth of highly selective sAC inhibitors usable in cellular contexts led to the screening of a combinatorial chemical library for small molecules capable of inhibiting sAC (see Example 11 and Table 1). A compound, KH7, which potently inhibited sAC (FIG. 9A) and was inert towards tmACs (FIG. 9C), was identified. A structurally similar compound, KH7.15, was inert towards both sAC (FIG. 9B) and tmACs (FIG. 9C) and is useful as a negative control.

Figure 9:
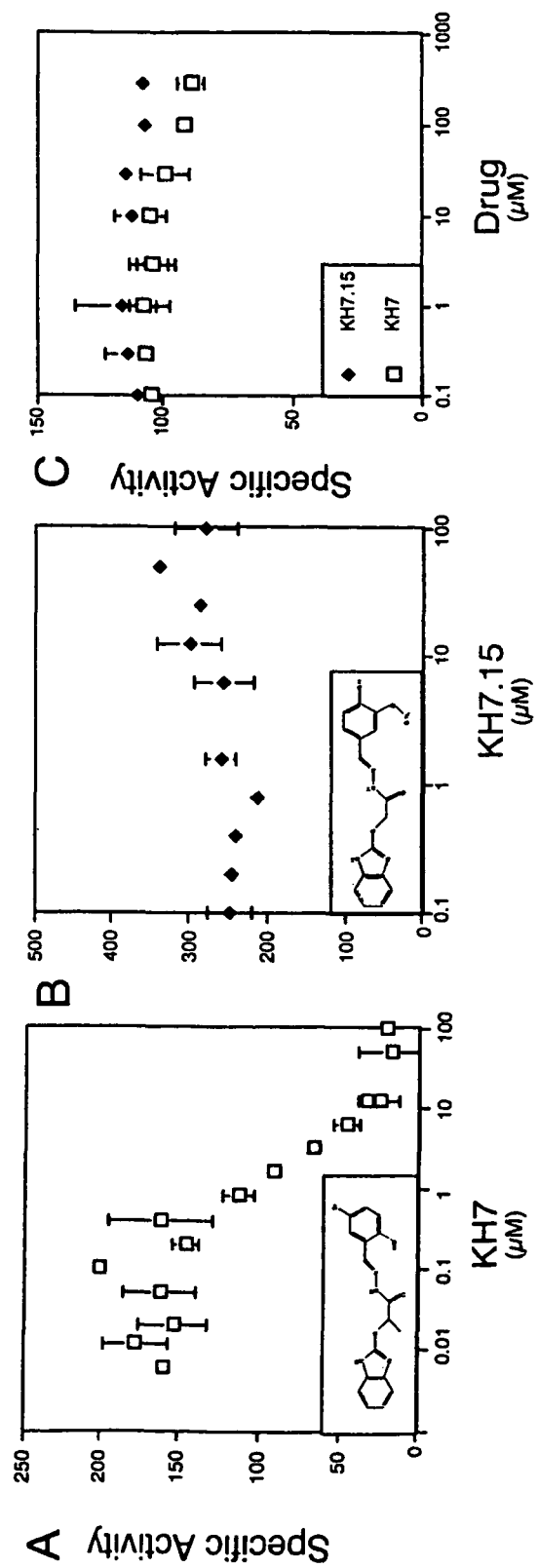
FIGS. 9A-C illustrate that KH7 differentiates between sAC and tmAC generated cAMP. In vitro cyclase activity of purified recombinant sAC in the presence of bicarbonate (40 mM) and calcium (0.5 mM) (FIGS. 9A-B) or INS-1E cell lysate stimulated by forskolin (10 µM) (FIG. 9C) in the presence of the indicated concentrations of KH7 (open squares, µM) (FIGS. 9A and 9C) or KH7.15 (closed diamonds, µM) (FIGS. 9B-C).
Figure 10:
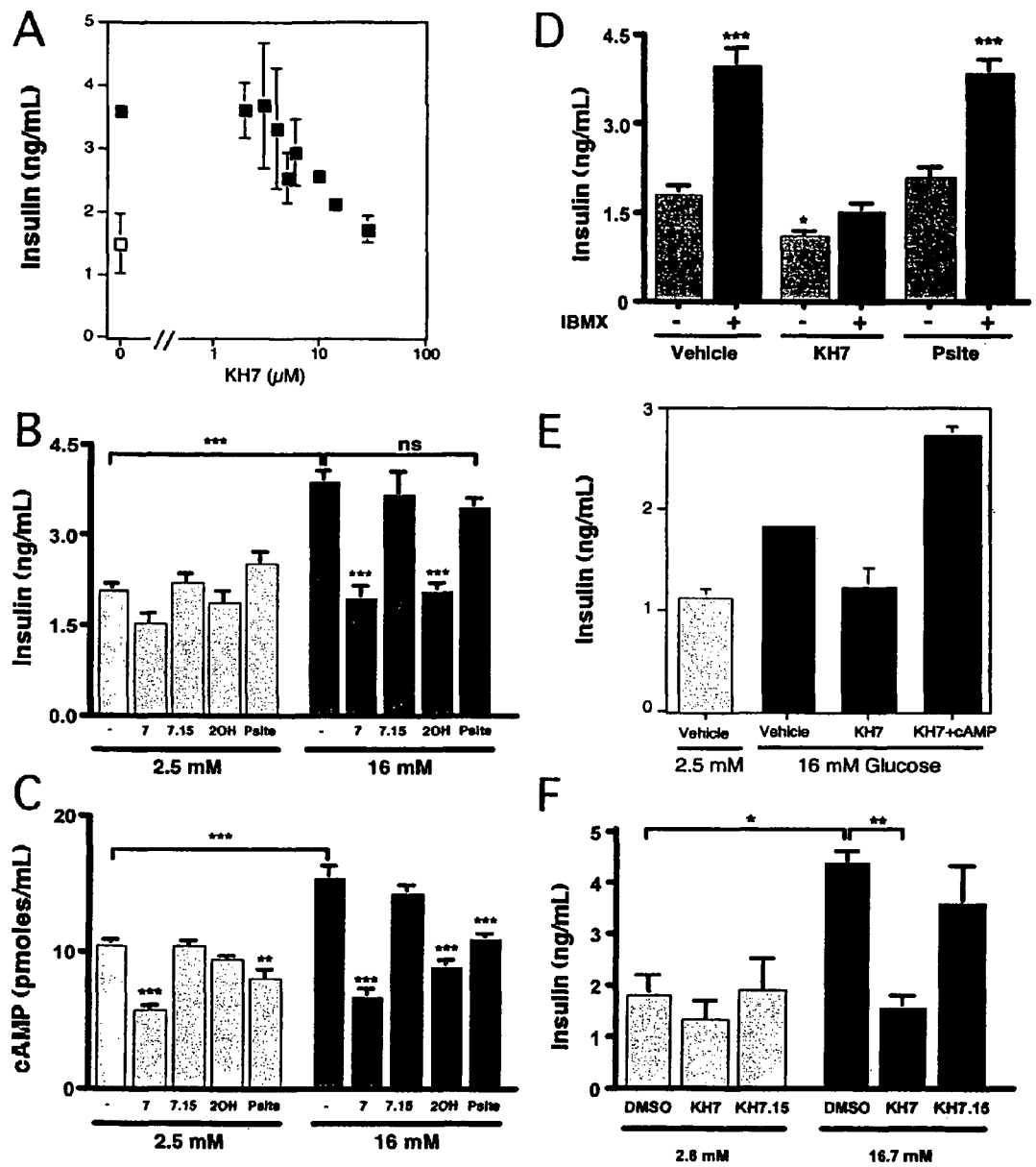
FIGS. 10A-F illustrate that sAC generated cAMP is necessary for glucose-stimulated insulin secretion (GSIS).
Figure 11:
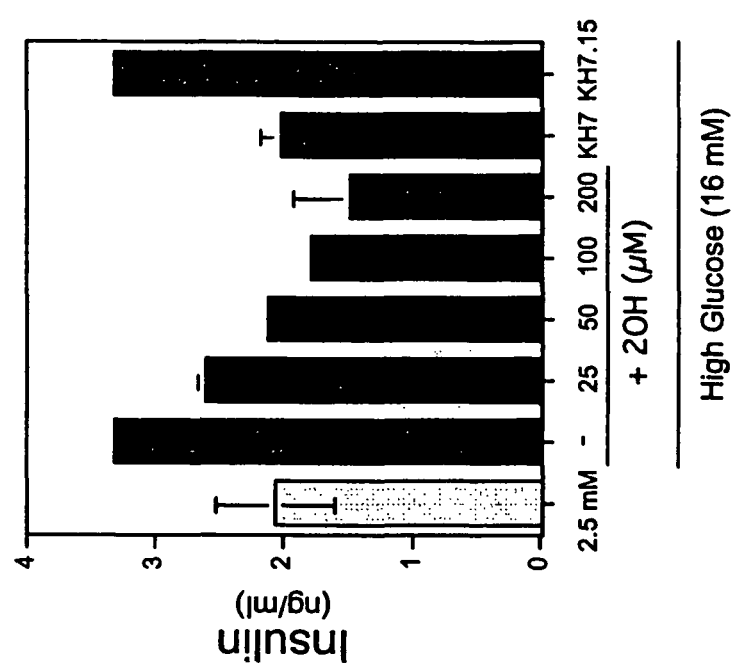
FIG. 11 illustrates that the catechol estrogen 2-hydroxyestradiol (2OH) inhibited GSIS in INS-1E insulinoma cells. The figure shows 15 minute insulin release from INS-1E cells incubated in low glucose (2.5 mM, lightly shaded bar) or high glucose (16 mM) with indicated concentrations of 2-hydroxyestradiol (2OH; first five darkly shaded bars from the left), KH7 (30 µM; sixth darkly shaded bar from the left) or KH7.15 (30 µM; seventh darkly shaded bar from the left). Shown is a representative experiment repeated at least twice; values represent averages of duplicate determinations with standard deviations indicated.

Incubation in low glucose (i.e., 2.5 mM) elicits a basal level of insulin secretion from INS-1E cells (Merglen et al., "Glucose Sensitivity and Metabolism-Secretion Coupling Studied During Two-Year Continuous Culture in INS-1E Insulinoma Cells," *Endocrinology* 145:667-678 (2004), which is hereby incorporated by reference in its entirety), whereas incubation in high glucose (i.e., 16 mM) led to an elevated level of insulin release (FIGS. 10A-F). This increased insulin release is termed glucose-stimulated insulin secretion (GSIS). KH7 dose dependently inhibited GSIS with an $IC_{50}$ (~5 µM) (FIG. 10A) similar to its potency on purified sAC protein (FIG. 9A: $IC_{50}$~3 µM). KH7 blocked all insulin release induced by high glucose, while the structurally related, inert KH7.15 did not affect insulin secretion (FIG. 10B). In the presence of KH7, no significant insulin release was observed up to 45 minutes after addition of high glucose. A structurally unrelated, noncompetitive inhibitor of sAC, 2-hydroxyestradiol (CE) (Braun, "Inhibition of the Soluble Form of Testis Adenylate Cyclase by Catechol Estrogens and Other Catechols," *Proc. Soc. Exp. Biol. Med.* 194:58-63 (1990); Pastor-Soler et al., "Bicarbonate-Regulated Adenylyl Cyclase (sAC) is a Sensor That Regulates pH-Dependent V-ATPase Recycling," *J. Biol. Chem.* 278: 49523-49529 (2003), which are hereby incorporated by reference in their entirety), also completely inhibited GSIS (FIG. 10B and FIG. 11). Furthermore, specific inhibition of tmACs by P site inhibitors did not have any significant affect on insulin release (FIG. 10B); therefore, cyclase specific inhibition revealed that sAC is the only adenylyl cyclase required for GSIS.

It was genetically confirmed that sAC is required for GSIS, using RNAi knockdown. Transfection of two distinct sAC-specific RNAi oligonucleotides reduced sAC protein levels (FIG. 12A, insert) and blunted GSIS (FIG. 12B).

Concomitant with its induction of insulin secretion, glucose elicits a rise in intracellular cAMP in beta-cells (Charles et al., "Adenosine 3',5'-Monophosphate in Pancreatic Islets: Glucose-Induced Insulin Release," *Science* 179: 569-571 (1973); Charles et al., "Insulin Secretion. Interrelationships of Glucose, Cyclic Adenosine 3:5-Monophosphate, and Calcium," *J. Biol. Chem.* 250:6134-6140 (1975); Rutter, "Nutrient-Secretion Coupling in the Pancreatic Islet Beta-Cell: Recent Advances," *Mol. Aspects Med.* 22:247-284 (2001), which are hereby incorporated by reference in their entirety). sAC-specific RNAi (FIG. 12A), KH7 or 2-hydroxyestradiol, but not KH7.15 (FIG. 10C), blocked the cAMP induced by the presence of high glucose. As with insulin secretion (FIG. 10A), KH7's $IC_{50}$ for blocking glucose-induced cAMP matched its dose response of sAC inhibition (FIG. 9A). Although inert towards GSIS (FIG. 10B), P site inhibitor partially decreased glucose-induced cAMP generation (FIG. 10C). This decrease is consistent with inhibition of tmAC type VIII, known to be present in beta-cells and previously shown to be responsive to glucose-induced elevations of calcium (Delmeire et al., "Type VIII Adenylyl Cyclase in Rat Beta Cells: Coincidence Signal Detector/Generator for Glucose and GLP-1," *Diabetologia* 46:1383-1393 (2003), which is hereby incorporated by reference in its entirety). However, as confirmed below, tmAC-generated cAMP is ineffective at initiating insulin secretion (Delmeire et al., "Type VIII Adenylyl Cyclase in Rat Beta Cells: Coincidence Signal Detector/Generator for Glucose and GLP-1," *Diabetologia* 46:1383-1393 (2003); Ma et al., "Constitutively Active Stimulatory G-Protein Alpha S in Beta-Cells of Transgenic Mice Causes Counterregulation of the Increased Adenosine 3',5'-Monophosphate and Insulin Secretion," *Endocrinology* 134:42-47 (1994); Rutter, "Nutrient-Secretion Coupling in the Pancreatic Islet Beta-Cell: Recent Advances," *Mol. Aspects Med.* 22:247-284 (2001), which are hereby incorporated by reference in their entirety).

In cells, cAMP levels are determined by their synthesis via adenylyl cyclases and their breakdown via phosphodiesterases (PDE). Therefore, the ability of the global PDE inhibitor IBMX to increase cAMP levels is dependent upon the presence of an active cyclase. IBMX enhanced GSIS at least 2 fold in INS-1E cells (FIG. 10D), but in contrast to exogenously added, membrane permeable cAMP analogs (FIG. 10E), IBMX treatment did not restore GSIS in the presence of KH7 inhibition (FIG. 10D). Thus, IBMX could not rescue GSIS in the absence of a source of second messenger, confirming that the sole source of glucose-induced cAMP capable of initiating insulin release is KH7 sensitive sAC.

The ability of KH7 to block both cAMP generation and insulin secretion was not due to cellular toxicity; the cells appeared healthy, and inhibition was specific, selective, and reversible. Insulin release induced by the phorbol ester PMA was unaffected by KH7 (FIGS. 13A-B), and KH7 inhibition of GSIS was rescued by addition of a membrane-permeable cAMP analog (FIG. 10E). These data show that the transduction pathways essential for insulin release were still functional in KH7 treated cells. Sixty minutes following removal of drug (i.e., drug "washout"), normal GSIS was restored, demonstrating that there were no significant, long-lasting changes induced by KH7 treatment. Finally, transferrin recycling (Johnson et al., "A Di-Leucine Sequence and a Cluster of Acidic Amino Acids are Required for Dynamic Retention in the Endosomal Recycling Compartment of Fibroblasts," *Mol. Biol. Cell* 12:367-381 (2001), which is hereby incorporated by reference in its entirety) in INS-1E cells was unaffected by KH7 (FIG. 13B) or CE; therefore, inhibition of sAC did not have pleiotropic effects on general vesicular trafficking to the cell surface.

To establish the role of sAC inhibitors in a more native beta-cell preparation, experiments were performed to investigate whether these small molecules would affect GSIS in primary mouse islets. KH7 (FIG. 10F) and CE inhibited insulin release induced by high glucose in mouse primary islets.

sAC-Generated cAMP is Sufficient to Elicit Insulin Secretion

The genetic and pharmacological inhibitor studies revealed that sAC-generated cAMP is necessary for GSIS; next, it was demonstrated that, distinct from tmAC-generated cAMP, sAC-generated cAMP was sufficient to elicit insulin secretion. Consistent with published reports (Delmeire et al., "Type VIII Adenylyl Cyclase in Rat Beta Cells: Coincidence Signal Detector/Generator for Glucose and GLP-1," *Diabetologia* 46:1383-1393 (2003); Ma et al., "Constitutively Active Stimulatory G-Protein Alpha S in Beta-Cells of Transgenic Mice Causes Counterregulation of the Increased Adenosine 3',5'-Monophosphate and Insulin Secretion," *Endocrinology* 134:42-47 (1994); Rutter, "Nutrient-Secretion Coupling in the Pancreatic Islet Beta-Cell: Recent Advances," *Mol. Aspects Med.* 22:247-284 (2001), which are hereby incorporated by reference in their entirety), in low glucose, stimulation of tmACs by hormones, i.e., glucagon (FIG. 14A) or GLP-1, elicited a three fold increase in cAMP generation, but led to no significant increase in insulin release (FIG. 14A). In contrast, stable overexpression of sAC in INS-1E cells (FIG. 14B, inset) elevated both intracellular cAMP and insulin secretion even in low glucose (FIG. 14B). This sAC overexpression-induced increase in insulin release was inhibited by KH7 and sAC overexpression potentiated GSIS in a KH7 dependent manner (FIG. 14C). Therefore, sAC generated cAMP is distinct from tmAC-generated cAMP; tmAC generated cAMP is only capable of modulating GSIS (Delmeire et al., "Type VIII Adenylyl Cyclase in Rat Beta Cells: Coincidence Signal Detector/Generator for Glucose and GLP-1," *Diabetologia* 46:1383-1393 (2003); Rutter, "Nutrient-Secretion Coupling in the Pancreatic Islet Beta-Cell: Recent Advances," *Mol. Aspects Med.* 22:247-284 (2001), which are hereby incorporated by reference in their entirety), while sAC generated cAMP is uniquely capable of initiating insulin secretion by itself.

sAC Inhibition Induces a Diabetes-Like Phenotype in Mice

The observed role of sAC in insulin release in an animal was confirmed by performing a glucose tolerance test on mice injected with KH7 or with vehicle control. Mice injected with KH7 were glucose intolerant as compared to mice injected with vehicle alone (FIG. 15A); blood glucose reached higher levels after KH7 injection. Furthermore, whereas a glucose challenge elicited the expected increase in serum insulin levels in control mice, no statistically significant glucose-induced insulin release was detected at any time following glucose challenge in mice injected with KH7 (FIG. 15B). KH7 did not appear to be toxic to the mice. Injection of KH7 (as well as vehicle control) did not elicit any behavior or stressful responses inconsistent with a simple saline injection. Complete anatomical, histological, and blood post-mortem analysis (performed within 48 hours after drug treatment) revealed no significant toxicology or histological pathology associated with a single injection of KH7. There were no long-term pancreatic effects due to a single KH7 injection. One week after mice were injected with KH7 and displayed delayed glucose tolerance and blunted insulin release, these same mice (n=2) exhibited a normal glucose tolerance and insulin response in a glucose tolerance test in the absence of further drug. Therefore, a sAC specific inhibitor which blocked GSIS in cell lines and primary islets elicited a transient diabetes-like phenotype in mice.

In summary, it is likely that sAC senses intrinsic cellular signals originating from glucose metabolism (Zippin et al., "CO(2)/HCO(3)(-)-Responsive Soluble Adenylyl Cyclase as a Putative Metabolic Sensor," *Trends Endocrinol. Metab.* 12:366-370 (2001), which is hereby incorporated by reference in its entirety) to initiate cAMP-dependent pathways essential for GSIS. In contrast, tmACs are responsible for the cAMP-dependent potentiation of GSIS (Delmeire et al., "Type VIII Adenylyl Cyclase in Rat Beta Cells: Coincidence Signal Detector/Generator for Glucose and GLP-1," *Diabetologia* 46:1383-1393 (2003); Rutter, "Nutrient-Secretion Coupling in the Pancreatic Islet Beta-Cell: Recent Advances," *Mol. Aspects Med.* 22:247-284 (2001), which are hereby incorporated by reference in their entirety). The role of sAC as a glucose sensor in beta-cells raises the possibility that it also senses nutritional availability in other physiological systems. Consistent with this hypothesis, conservation of bicarbonate-responsive sAC-like cyclases from bacteria (Cann et al., "A Defined Subset of Adenylyl Cyclases is Regulated by Bicarbonate Ion," *J. Biol. Chem.* 278: 35033-35038 (2003); Chen et al., "Soluble Adenylyl Cyclase as an Evolutionarily Conserved Bicarbonate Sensor," *Science* 289:625-628. (2000), which are hereby incorporated by reference in their entirety) and unicellular eukaryotes (Roelofs et al., "Deducing the Origin of Soluble Adenylyl Cyclase, A Gene Lost in Multiple Lineages," *Mol. Biol. Evol.* 19:2239-2246 (2002), which is hereby incorporated by reference in its entirety) suggest that this class of cyclase represents an evolutionarily conserved mechanism for sensing environmental cues such as pH and nutritional availability. In contrast, G protein-regulated tmACs are first documented in the social amoeba Dictyostelium (Pitt et al., "Structurally Distinct and Stage-Specific Adenylyl Cyclase Genes Play Different Roles in Dictyostelium Development," *Cell* 69:305-315 (1992), which is hereby incorporated by reference in its entirety), and therefore, seem to have arisen concomitant with the need for intercellular communication.

This study also demonstrates the strategic use of adenylyl cyclase selective inhibitors to identify sAC as the source of cAMP mediating GSIS. Their use constitutes a general paradigm for differentiating between sAC and tmACs as the originator of this ubiquitous second messenger implicated in a wide variety of physiological processes.

Diseases whose predisposing factor is a pathologically uncontrolled release of insulin (e.g., insulinoma or persistent hyperinsulinemic hypoglycemia) can lead to life threatening episodes of hypoglycemia possibly resulting in stroke, organ failure, or even death. With its transient effects on insulin release and lack of toxicity, KH7 represents a potential therapeutic for the treatment of hyperinsulinemia or hypoglycemia. Finally, because sAC is important for normal glucose-stimulated insulin secretion and glucose homeostasis in mice and because overexpression of sAC is sufficient to elicit insulin secretion, sAC activators may represent a new class of diabetes therapeutics.

Example 16

Inhibition of *Plasmodium falciparum* sAC-Like Adenylyl Cyclase—A New Mechanism for a Malaria Antibiotic The causative agent of malaria, *Plasmodium falciparum*, expresses two adenylyl cyclase genes (Muhia et al., "Multiple Splice Variants Encode a Novel Adenylyl Cyclase of Possible Plastid Origin Expressed in the Sexual Stage of the Malaria Parasite *Plasmodium falciparum*," *J. Biol. Chem.*, 278(24):22014-22022 (2003), which is hereby incorporated by reference in its entirety), which were both postulated to be bicarbonate responsive based upon the presence of a predictive threonine residue (Muhia et al., "Multiple Splice Variants Encode a Novel Adenylyl Cyclase of Possible Plastid Origin Expressed in the Sexual Stage of the Malaria Parasite *Plasmodium falciparum*," *J. Biol. Chem.*, 278(24): 22014-22022 (2003); Cann et al., "A Defined Subset of Adenylyl Cyclases is Regulated by Bicarbonate Ion," *J. Biol. Chem.*, 278(37):35033-35038 (2003), which are hereby incorporated by reference in their entirety). One gene, PfACb, conforms to the mammalian sAC structure; it possesses two catalytic domains related to C1 and C2 of mammalian sAC, followed by a consensus P loop sequence (Muhia et al., "Multiple Splice Variants Encode a Novel Adenylyl Cyclase of Possible Plastid Origin Expressed in the Sexual Stage of the Malaria Parasite *Plasmodium falciparum,*" *J. Biol. Chem.,* 278(24):22014-22022 (2003), which is hereby incorporated by reference in its entirety). The other, PfACa, is most similar to single domain cyanobacterial adenylyl cyclases. However, both differ significantly from the amino acid sequence of mammalian sAC, suggesting that PfAC selective inhibitors can be developed.

The dependence upon $CO_2$/bicarbonate for culturing *Plasmodium falciparum* (Trager et al., "Human Malaria Parasites in Continuous Culture, *Science,* 193(4254):673-675 (1976), which is hereby incorporated by reference in its entirety) and the identification of two sAC-like adenylyl cyclases predicted to be bicarbonate responsive (Muhia et al., "Multiple Splice Variants Encode a Novel Adenylyl Cyclase of Possible Plastid Origin Expressed in the Sexual Stage of the Malaria Parasite *Plasmodium falciparum,*" *J. Biol. Chem.,* 278(24):22014-22022 (2003), which is hereby incorporated by reference in its entirety) suggested that bicarbonate regulation of one (or both) of these cyclases may be essential for viability. It can be reasoned that the sAC inhibitor, KH7, which was found to inhibit sAC-like adenylyl cyclases from evolutionarily distant organisms including, mammals, Chloroflexus, Cyanobacteria, and *Candida*, should also inhibit the sAC-like PfAC cyclases. Therefore, the effect of sAC inhibitors on *P. falciparum* viability was tested. Using a viability assay based on the luminescence of a strain of *P. falciparum* engineered to express luciferase, it was demonstrated that infectious growth (i.e., in red blood cells) was rapidly (in a single generation) and potently affected by KH7 (FIG. 16A). The most likely molecular target of KH7 in *P. falciparum* are the sAC-like PfAC cyclases. The ability of KH7 to inhibit adenylyl cyclase activity in whole cell extracts of isolated parasites was confirmed. Following the procedure of Read and Mikkelsen, "*Plasmodium falciparum*-Infected Erythrocytes Contain an Adenylate Cyclase with Properties Which Differ from the Host Enzyme," *Molecular & Biochemical Parasitology,* 45:109 (1991), which is hereby incorporated by reference in its entirety, for isolating parasites and specifically assaying parasite adenylyl cyclase activity, it was demonstrated that KH7 displayed equal dose responses at killing parasites and at inhibiting PfAC activity (FIG. 16B). These data strongly support the hypothesis that at least one of the PfAC genes is essential for viability and represents a novel target for malaria therapeutics. In addition, it was found that the compound used as a negative control in mammalian contexts, KH7.15, displayed a 10-fold lower affinity for killing *P. falciparum* and for inhibiting PfAC activity relative to KH7. Therefore, because KH7.15 does not inhibit mammalian sAC yet does inhibit PfACs and is lethal to parasites, it provides proof-of-principle that PfAC inhibitors can be developed which distinguish between mammalian and plasmodium sAC-like adenylyl cyclases. Since relative high doses of KH7.15 (≥100 µM) are required to inhibit PfAC activity and kill parasites, there is a likelihood for other side effects, unrelated to mammalian sAC. Thus, it would be advantageous to identify a drug that will kill *P. falciparum* in mammalian blood, while having little, if any, inhibitory effect on mammalian sAC and biological effects on the human host that are mediated by mammalian sACs. KH7 or KH7.15 are suitable lead compounds for development of a new PfAC inhibitor that will kill PfAC selectively and thus provide an avenue to the eradication of the malaria parasite within mammalian systems.

Example 17

Inhibition of *Candida albicans* sAC-Like Adenylyl Cyclase—A New Mechamisn for a *Candida albicans* Antibiotic

*Candida albicans* is the most common opportunistic fungal pathogen of humans accounting for up to 60% of *Candida* species isolated from cases of infection. The increase in the numbers of patients in the high-risk category, i.e., those requiring long-term in-dwelling catheters, broad-spectrum antibiotic therapy, and treatment for cancer have all contributed to the escalation in the prevalence of serious *Candida* infections. *Candida albicans* expresses a sAC-like adenylyl cyclase gene and exhibits a strong dependence upon carbon dioxide (and bicarbonate, the activator of sAC-like adenylyl cyclases) for differentiation into the infectious part of its life cycle.

Figure 17A:
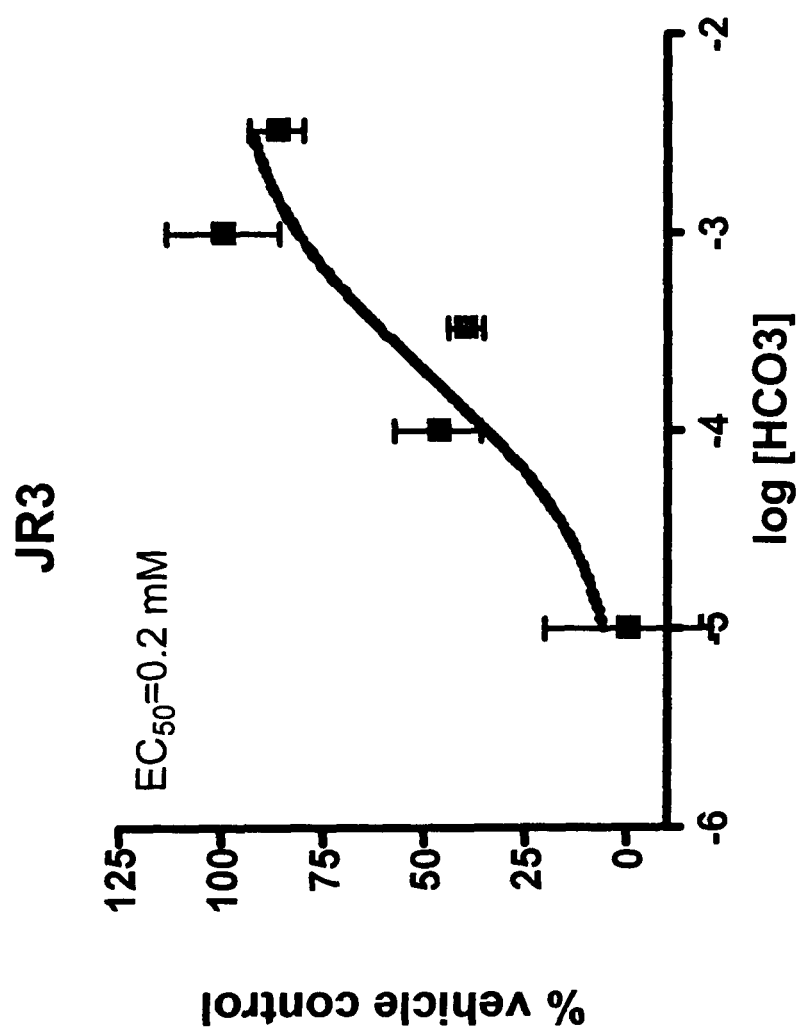
FIGS. 17A-B illustrate that the catalytic portion of the sAC-like adenylyl cyclase from *Candida albicans* (fragment JR3) is bicarbonate responsive and KH7 sensitive.

The catalytic portion of the sAC like adenylyl cyclase from *Candida albicans* (fragment JR3) was cloned, expressed, and purified, and experiments were performed, showing that the JR3 fragment was bicarbonate responsive and KH7 sensitive. FIG. 17A illustrates the bicarbonate dependence of the JR3 fragment; bicarbonate stimulated the adenylyl cyclase activity with an $EC_{50}$ of approximately 0.2 mM. FIG. 17B illustrates the KH7 sensitivity of the JR3 fragment; the sAC inhibitor, KH7, inhibited the expressed and purified *candida* sAC-like adenylyl cyclase with an $IC_{50}$ of approximately 23 µM. KH7 also dose dependently inhibited the $CO_2$ induced differentiation into the filamentous, infectious stage with similar dose dependency.

Example 18

Role of sAC in NGF-Induced Rap1 Activation

Neurotrophic factors, or neurotrophins, are a family of proteins whose principal functions include promoting differentiation and survival of multiple neuronal subtypes in the central and peripheral nervous systems. Recently, alterations in neurotrophin-mediated signaling have been implicated in the progression of several devastating neurodegenerative diseases. In particular, studies in cell and animal models have identified nerve growth factor (NGF), the most studied member of the neurotrophin family, as a key player in the pathogeneses of Alzheimer's disease (AD), amyotrophic lateral sclerosis (ALS), and peripheral neuropathies (Dichter et al., "Nerve Growth Factor-Induced Increase in Electrical Excitability and Acetylcholine Sensitivity of a Rat Pheochromocytoma Cell Line," *Nature,* 268:501-504 (1977), which is hereby incorporated by reference in its entirety).

One of the most widely used systems for dissecting the biology of NGF is the pheochromocytoma PC12 cell line; upon treatment with NGF, PC12 cells differentiate into sympathetic-like neurons. Among the early steps known to be in this signaling pathway is the activation of the small G protein Rap1. Interestingly, both phenomena, neuronal differentiation and Rap1 activation, can be induced by cell-permeable analogues of cAMP (Heidemann et al., "Synergistic Effects of Cyclic AMP and NGF on Neurite Outgrowth and MT Stability of PC 12 Cells," *J. Cell Biol,* 916-927 (1985); Vossler et al., "cAMP Activates MAP Kinase and Elk-1 Through a B-Raf and Rap1-Dependent Pathway," *Cell,* 89(1):73-82 (1997), which are hereby incorporated by reference in their entirety). Also like NGF, cAMP has been found to be essential for axonal regeneration after nerve injury and associated with neurodegenerative processes (Dubus et al., "Expression of Trk Isoforms in Brain Regions and in the Striatum of Patients With Alzheimer's Disease," *Exp. Neurol.*, 165(2):285-294 (2000); Salehi et al., "Alzheimer's Disease and NGF Signaling," *J. Neural Trans.*, 111:323-345 (2004); Turner et al., "Effect of p75 Neurotrophin Receptor Antagonist on Disease Progression in Transgenic Amyotrophic Lateral Sclerosis Mice." *J. Neurosci. Res.*, 78:193-199 (2004), which are hereby incorporated by reference in their entirety). These findings suggest a link between NGF and the second messenger; however, the mechanism leading from NGF to cAMP has never been described.

Figure 17:
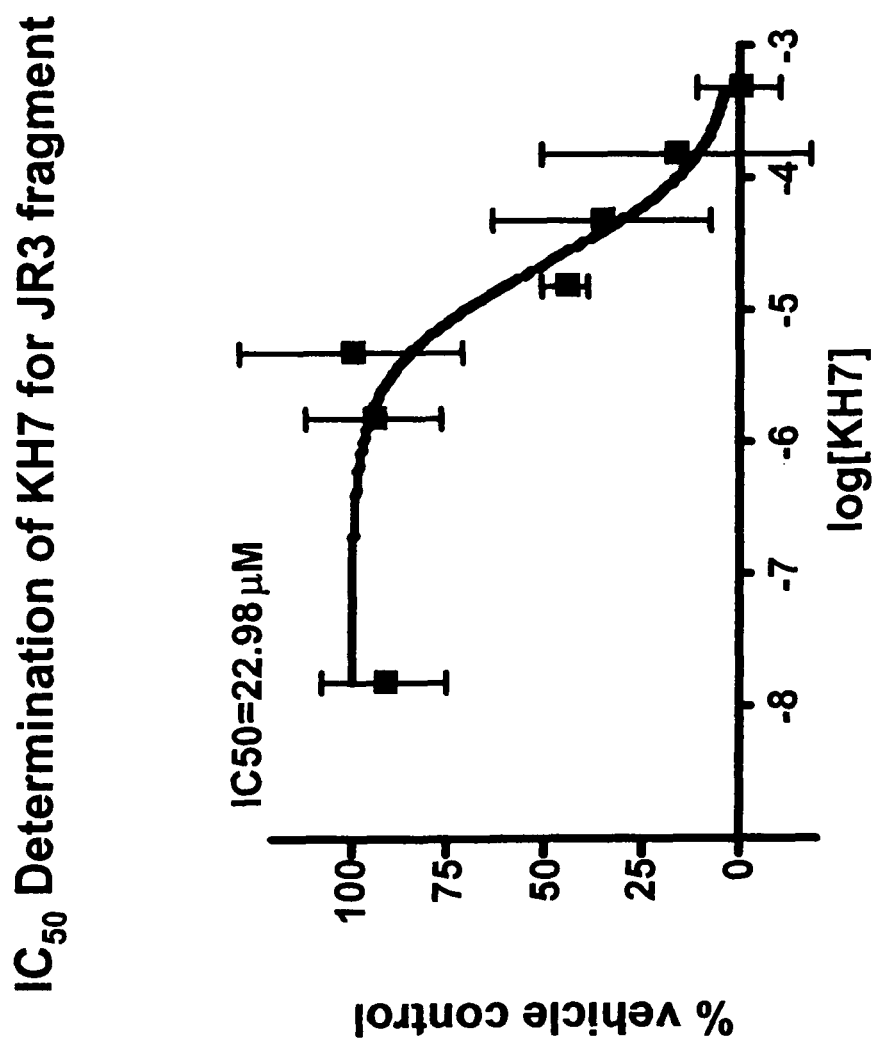
Figure 18:
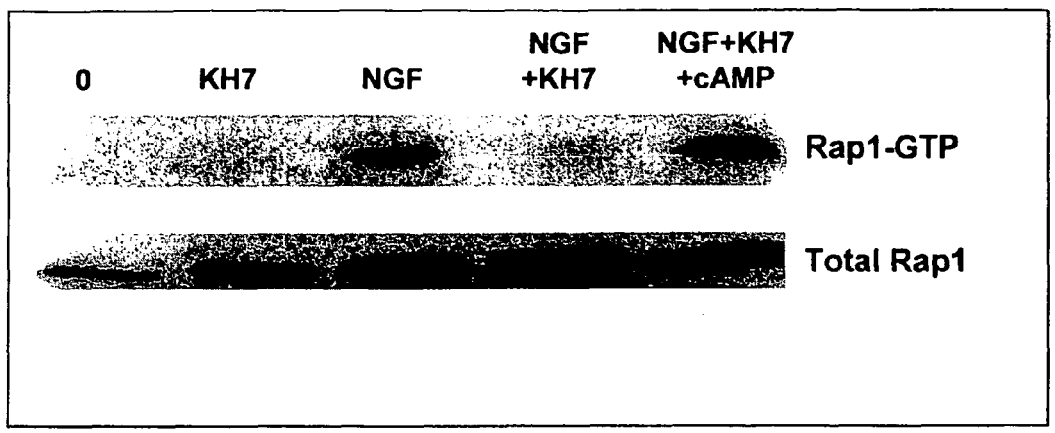
FIG. 18 illustrates that NGF induced Rap1 activation is blocked by KH7 and rescued by membrane permeable cAMP. PC12 cells were stimulated with or without nerve growth factor (NGF) for 15 minutes in the presence or absence of KH7 (50 µM) and 1 mM 8Br-cAMP. Top panel shows activated Rap1 (GTP bound Rap1) isolated from whole cell extracts by "pull-down" with Rap-GTP binding domain of RalGDS; bottom panel shows total Rap1 in extract (both GTP bound and GDP bound) as control.

The sAC-specific inhibitor, KH7, was found to block NGF induced Rap1 activation (FIG. 17), suggesting that sAC is required for NGF induced Rap1 activation. Rap1 activation can be restored by addition of exogenous cAMP, confirming that KH7 is likely to mediate its effects solely via inhibition of sAC. These data demonstrate that sAC is an integral signaling protein in the differentiation and survival of neurons, and suggest that sAC may prove to be a novel therapeutic target for the treatment of AD, ALS or peripheral neuropathies.

Although the invention has been described in detail, for the purpose of illustration, it is understood that such detail is for that purpose and variations can be made therein by those skilled in the art without departing from the spirit and scope of the invention which is defined by the following claims.

What is claimed:

1. A method of inhibiting adenylyl cyclase of a eukaryotic parasite in a mammal, the method comprising:
contacting said eukaryotic parasite in said mammal with a compound having the following formula:

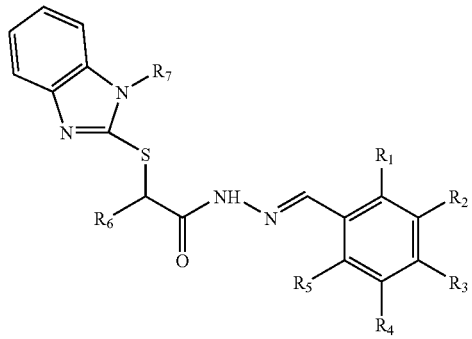

wherein:
$R_1$ is H, OH, alkyloxy, or halogen;
$R_2$ and $R_5$ are H or halogen;
$R_3$ is H or OH;
$R_4$ is H, alkyloxy, or halogen;
$R_6$ is alkyl; and
$R_7$ is H or $CH_2R_8$, wherein $R_8$ is H, alkyl, or substituted or unsubstituted phenyl,
with the proviso that at least one of $R_1$, $R_2$, and $R_4$ is a halogen.

2. The method of claim 1, wherein the mammalian cell is a human.

3. The method of claim 1, wherein the eukaryotic parasite is a fungal organism.

4. The method according to claim 1, wherein the compound has the following formula:

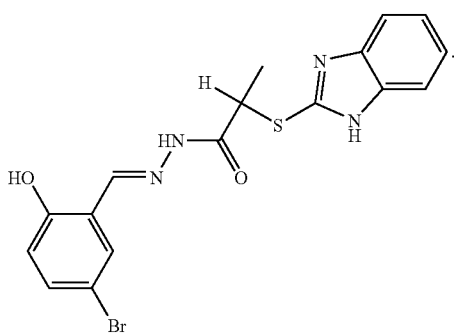 [SMILES: CC(Sc1nc2ccccc2[nH]1)C(=O)N/N=C/c1cc(Br)ccc1O]

5. The method of claim 3, wherein the compound has the following formula:

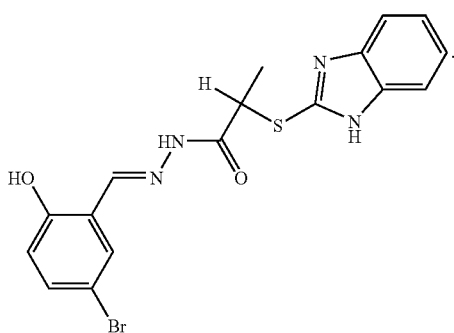 [SMILES: CC(Sc1nc2ccccc2[nH]1)C(=O)N/N=C/c1cc(Br)ccc1O]

* * * * *